(12) United States Patent
Lowery et al.

(10) Patent No.: US 8,546,536 B2
(45) Date of Patent: Oct. 1, 2013

(54) GENETICALLY ENGINEERED G-ALPHA PROTEINS AND USES THEREOF

(75) Inventors: Robert G. Lowery, Belleville, WI (US); Thomas K. Zielinski, Fitchburg, WI (US)

(73) Assignee: Bellbrook Labs, LLC, Madison, WI (US)

( * ) Notice: Subject to any disclaimer, the term of this patent is extended or adjusted under 35 U.S.C. 154(b) by 217 days.

(21) Appl. No.: 13/060,895

(22) PCT Filed: Aug. 28, 2009

(86) PCT No.: PCT/US2009/055438
§ 371 (c)(1), (2), (4) Date: May 6, 2011

(87) PCT Pub. No.: WO2010/025417
PCT Pub. Date: Mar. 4, 2010

(65) Prior Publication Data
US 2011/0212476 A1    Sep. 1, 2011

Related U.S. Application Data

(60) Provisional application No. 61/093,184, filed on Aug. 29, 2008.

(51) Int. Cl.
*C07K 1/00* (2006.01)
*C12N 9/00* (2006.01)
*C12N 9/14* (2006.01)

(52) U.S. Cl.
USPC .......................... 530/350; 435/183; 435/195

(58) Field of Classification Search
None
See application file for complete search history.

(56) References Cited

U.S. PATENT DOCUMENTS
2006/0172335 A1    8/2006  Lowery et al.

FOREIGN PATENT DOCUMENTS
WO    2010025417    3/2010

OTHER PUBLICATIONS

Hinrichs et al. (Journal of Cellular Biochemistry 93:409-417 (2004)).*
Zielinski et al. "An RGS protein HTS assay strategy using the transcreenerTM GDP assay" Apr. 10, 2008, Retrieved from the Internet: URL:http://www.bellbrooklabs.com/PDFs/SBS2008RGS.pdf [retrieved on Nov. 2, 2009] ; & anomymous: "SBS 14th annual conference and exhibition" Apr. 1, 2008, Retrieved from the Internet: URL:http://www.sbsonline.com/sbscon/2008/tech/keynotes.php [retrieved on Nov. 2, 2009].
Roncinske et al. "An RGS protein HTS assay strategy using the TranscreenerTM GDP assay" Apr. 10, 2008, Retrieved from the Internet URL:http://www.conferencearchives.com/sbs/2008/abstracts/P11 004_a.php [retrieved on Nov. 2, 2009].
Posner B A et al: "The A326S mutant of G(i[alpha]1) as an approximation of the receptor-bound state" Journal of Biological Chemistry Aug. 21, 1998 US, vol. 273, No. 34, Aug. 21, 1998, pp. 21752-21758, ISSN: 0021-9258.
Berman D M et al: "Gaipand RGS4 Are GTPASE-Activating Proteins for the GI Subfamily of G Protein Allpha Subunits" Cell, Cell Press, Cambridge, MA, US, vol. 86, Aug. 9, 1996, pp. 445-452, XP002058372 ISSN: 0092-8674.
Coleman D E et al: "Structures of active conformations of Gi [alpha]1 and the mechanism of GTP hydrolysis" Science USA, vol. 265, No. 5177, Sep. 2, 1994, pp. 1405-1412, ISSN: 0036-8075.
Preliminary Report on Patentability and Written Opinion issued on Mar. 1, 2011 (International Patent Application No. PCT/US2009/055438, filed Aug. 28, 2009).
International Search Report mailed Nov. 13, 2009 (International Patent Application No. PCT/US2009/055438, filed Aug. 28, 2009).

* cited by examiner

*Primary Examiner* — Suzanne M Noakes
*Assistant Examiner* — Jae W Lee
(74) *Attorney, Agent, or Firm* — Quarles & Brady LLP

(57) ABSTRACT

The present invention relates to novel engineered Gα proteins and assay methods of using such proteins to advance drug discovery. Engineered Gα proteins described by the invention contain alterations of at least one and preferably two or more amino acid residues that are highly conserved among all four subfamilies of Gα proteins. A preferred engineered protein disclosed here is a double mutant, Gαπ R178M A326S. This specific combination of mutations yields an unexpectedly amplified effect on Gα function both in terms of GTPase activity (GTP hydrolysis) and GDP dissociation. This synergistic effect may have a profound influence on the way GPCR signaling pathways are examined for the development of new pharmacotherapies, particularly in the field of central nervous system disorders such as Parkinson's disease.

9 Claims, 7 Drawing Sheets

| | | | | | | | | | |
|---|---|---|---|---|---|---|---|---|---|
| DOUBLE MUTANT | -SNTYEEAA- | A···· | ···· | ···· | ···· | -YIQCQF | -EDLNKRKDT | -KEIYT--HF | TCSTDTKNVQ |
| Gaß | -SNTYEEAA- | A···· | ···· | ···· | ···· | -YIQCQF | -EDLNRRKDT | -KEIYT--HF | TCATDTKNVQ |
| Gai2 | -ANKYDEAA- | S···· | ···· | ···· | ···· | -YIQSKF | -EDLNKRKDT | -KEIYT--HF | TCATDTKNVQ |
| Gai1 | -SNTYEEAA- | A···· | ···· | ···· | ···· | -YIQCQF | -EDLNKRKDT | -KEIYT--HF | TCATDTKNVQ |
| Gai3 | -DPHCLRDVQ- | K···· | ···· | ···· | ···· | -FLVECF | -RNKR-RDQQ | QKPLYH--HF | TT-INTENVR |
| Gai2 | -DPHRLEDVQ- | R···· | ···· | ···· | ···· | -YLVQCF | -DRKR-RNRS | -KPLFH--HF | TT-IDTENVR |
| Gas | -YTTPEDAT- | PEPGEDPRVT | ···· | ···· | ···· | RAKYFIRDEF | LRIST-ASGD | -GRHYCYPHF | TCAVDTENIR |
| G8q11 | -PQRDAQAAR | E···· | ···· | ···· | ···· | -FIPKMF | -VDLNPDSD- | -KI-YS--HF | TCATDTENIR |
| Gaz | -QNTYEEAA- | V···· | ···· | ···· | ···· | -YIQRQF | -EDLNRNKET | -KEIYS--HF | TCATDTSNIR |
| Gaio | -PNTYEDAA- | A···· | ···· | ···· | ···· | -YIQAQF | -ESKN-RSPN | -KEIYC--HM | TCATDTNNIQ |
| DOUBLE MUTANT | FVFDAVTDVI | IKNNLKDCGL | FCGLF | | | | | | |
| Gaß | FVFDAVTDVI | IKNNLKECGL | ···Y | | | | | | |
| Gai2 | FVFDAVTDVI | IKNNLKDCGL | ···F | | | | | | |
| Gai1 | FVFDAVTDVI | IKNNLKDCGL | ···F | | | | | | |
| Gai3 | LVFRDVKDTI | LHDNLKQLML | ···Q | | | | | | |
| Gai2 | FVFHAVKDTI | LQENLKDIML | ···L | | | | | | |
| Gas | RVFNDCRDI- | QRMHLRQYEL | ···V | | | | | | |
| G8q11 | FVFAAVKDTI | LQLNLKEYNL | ···C | | | | | | |
| Gaz | FVFDAVTDVI | IQNNLKYIGL | ···Y | | | | | | |
| Gaio | VVFDAVTDI- | IANNLRGCGL | ···· | | | | | | |

FIG. 3C

```
ORIGIN
    1 atgggctgca cgctgagcgc cgaggacaag gcggcggtgg agcggagtaa gatgatcgac
   61 cgcaacctcc gtgaggacgg cgagaaggcg gcgcgcgagg tcaagctgct gctgctcggt
  121 gctggtgaat ctggtaaaag tacaattgtg aagcagatga aaattatcca tgaagctggt
  181 tattcagaag aggagtgtaa acaatacaaa gcagtggtct acagtaacac catccagtca
  241 attattgcta tcattagggc tatggggagg ttgaagatag actttggtga ctcagcccgg
  301 gcggatgatg cacgccaact ctttgtgcta gctggagctg ctgaagaagg ctttatgact
  361 gcagaacttg ctggagttat aaagagattg tggaaagata gtggtgtaca agcctgtttc
  421 aacagatccc gagagtacca gcttaatgat tctgcagcat actatttgaa tgacttggac
  481 agaatagctc aaccaaatta catcccgact caacaagatg ttctcagaac tagagtgaaa
  541 actacaggaa ttgttgaaac ccattttact ttcaaagatc ttcattttaa aatgtttgat
  601 gtggggaggtc agagatctga gcggaagaag tggattcatt gcttcgaagg agtgacggcg
  661 atcatcttct gtgtagcact gagtgactac gacctggttc tagctgaaga tgaagaaatg
  721 aaccgaatgc atgaaagcat gaaattgttt gacagcatat gtaacaacaa gtggtttaca
  781 gatacatcca ttatactttt tctaaacaag aaggatctct ttgaagaaaa aatcaaaaag
  841 agccctctca ctatatgcta tccagaatat gcaggatcaa acacatatga agaggcagct
  901 gcatatattc aatgtcagtt tgaagacctc aataaaagaa aggacacaaa ggaaatatac
  961 acccacttca catgtgccac agatactaag aatgtgcagt ttgtttttga tgctgtaaca
 1021 gatgtcatca taaaaaataa tctaaaagat tgtggtctct tttaa Translation ="MGCTLSAEDKAAVERSKMIDRNLREDGEKAAREVKLLLLGAGES

GKSTIVKQMKIIHEAGYSEEECKQYKAVVYSNTIQSIIAIIRAMGRLKIDFGDSARAD

DARQLFVLAGAAEEGFMTAELAGVIKRLWKDSGVQACFNRSREYQLNDSAAYYLNDLD

RIAQPNYIPTQQDVLRTRVKTTGIVETHFTFKDLHFKMFDVGGQRSERKKWIHCFEGV

TAIIFCVALSDYDLVLAEDEEMNRMHESMKLFDSICNNKWFTDTSIILFLNKKDLFEE

KIKKSPLTICYPEYAGSNTYEEAAAYIQCQFEDLNKRKDTKEIYTHFTCATDTKNVQF

VFDAVTDVIIKNNLKDCGLF"
```

FIG. 4

GENETICALLY ENGINEERED G-ALPHA PROTEINS AND USES THEREOF

CROSS-REFERENCE TO RELATED APPLICATIONS

This application represents the national stage application of International Application No. PCT/US2009/055438 filed Aug. 28, 2009, which claims priority to U.S. Provisional Application No. 61/093,184, filed Aug. 29, 2008, both of which are incorporated by reference herein for all purposes.

STATEMENT REGARDING FEDERALLY SPONSORED RESEARCH OR DEVELOPMENT

This invention was made with United States government support under grant number IR43NS059082-01 awarded by the following government agency: National Institute of Neurological Disorders and Stroke. The United States government has certain rights in this invention.

BACKGROUND OF THE INVENTION

G-protein-coupled receptors (GPCRs) are by far the most extensively validated class of therapeutic targets, and there remains tremendous potential for targeting new receptors and their downstream effectors [Neubig et al. *Nat Rev Drug Discov,* 2002. 1(3): p. 187-97; and Roth et al. *Curr Pharm Des,* 2006. 12(14): p. 1785-95]. There are over 900 distinct GPCRs encoded in the human genome, and aside from approximately 300 which are involved in odor and taste reception, it is thought that hundreds represent viable targets for therapeutic intervention. Over half of existing drugs are GPCR ligands, yet the total number of receptors that they target is less than 30 [Esbenshade, T. *G Protein-Coupled Receptors in Drug Discovery,* 2005. Taylor and Francis: p. 15-36]. The proven clinical utility of modulating GPCR signal transduction has sustained formidable efforts in the pharmaceutical industry to identify new GPCR-ligand pairs that control clinically relevant signaling pathways [Mertens et al. *Pharmacogenomics,* 2004. 5(6): p. 657-72; and Armbruster et al. *J Biol Chem,* 2004], as well as equally vigorous efforts to discover further components of the GPCR signaling machinery that have the potential to become therapeutic targets.

GPCRs are extensively involved in signal transduction in the nervous system, serving as receptors for the major classes of neurotransmitters including GABA, dopamine and serotonin. Most of the drugs used to treat neurological disorders, including pain relievers, antidepressants and anti-psychotics, exert their effects through GPCRs [Esbenshade, T. *G Protein-Coupled Receptors in Drug Discovery,* 2005. Taylor and Francis: p. 15-36]. These include dopamine and dopaminergic agents for the treatment of Parkinson's disease and cholinergic agents for the treatment of Alzheimer's disease. Of the 2.2 billion prescriptions issued for the top 200 drugs in 2003, 527 million were for drugs targeting GPCRs, and 147 million were for pain medications targeting an opioid receptor alone—more than the total prescriptions for any other single target class [Esbenshade, T. *G Protein-Coupled Receptors in Drug Discovery,* 2005. Taylor and Francis: p. 15-36]. Given their extensive role in neurotransmission, GPCR signal transduction pathways clearly represent promising targets for improving the treatment of neurodegenerative diseases. Moreover, development of strategies for modulating these pathways more selectively would expand the potential for more effective treatments.

The standard model of GPCR signal transduction had long been restricted to a three-component system: receptor, G protein and effector [Gilman, A. G. *Annu Rev Biochem,* 1987. 56: p. 615-49]. The receptor, a cell-surface protein that spans the membrane seven times, is coupled to a membrane-associated heterotrimeric complex that comprises a GTP-hydrolyzing $G\alpha$ subunit and a $G\beta\gamma$ dimeric partner. Agonist-induced conformational changes enhance the guanine-nucleotide-exchange activity of the receptor, leading to the release of GDP (and subsequent binding of GTP) by the $G\alpha$ subunit depicted in FIG. 1. On binding GTP, conformational changes within the three 'switch' regions of $G\alpha$ allow the release of $G\beta\gamma$. Separated $G\alpha$·GTP and $GP\beta\gamma$ subunits are thus free to propagate signaling forward via separate (and sometimes converging) interactions with adenylyl cyclases, phospholipase-C (PLC) isoforms, potassium and calcium ion channels, guanine-nucleotide exchange factors for the small GTPase RhoA, and other effector systems (FIG. 1). The intrinsic GTP hydrolysis (GTPase) activity of $G\alpha$ resets the cycle by forming $G\alpha$·GDP, which has low affinity for effectors but high affinity for $G\beta\gamma$. In this way, the inactive, GDP-bound heterotrimer ($G\alpha\beta\gamma$) is reformed and capable once again to interact with activated receptor.

Based on this cycle of GTP exchange and hydrolysis, the duration of heterotrimeric G-protein signaling is thought to be controlled by the lifetime of the $G\alpha$ subunit in its GTP-bound state. It is precisely this interaction and the lifetime of the $G\alpha$-GTP complex which controls the extent and duration of the signal induced. If a pharmaceutical effector is to exert its most favorable response, optimization of the lifetime of signal transduction would be paramount. There is benefit in having the ability to control and possibly extend the lifetime of the $G\alpha$-GTP complex, and in doing so, the duration of the signaling response. The invention described here below in the detailed description section of the invention was designed to address this need.

In 1996, Dr. Siderovski's group [Siderovski et al. *Curr Biol,* 1996. 6(2): p. 211-2], along with other laboratories [Dohlman et al. *Mol Cell Biol,* 1996. 16(9): p. 5194-209; and Druey et al. *Nature,* 1996. 379(6567): p. 742-6] independently identified a superfamily of RGS ("regulator of G-protein signaling") proteins that bind $G\alpha$ subunits via a ~120 amino-acid RGS domain and dramatically accelerate their GTPase activity (GAP activity) [Hunt et al. *Nature,* 1996. 383(6596): p. 175-7; and Watson et al. *Nature,* 1996. 383 (6596): p. 172-5], thereby attenuating heterotrimer-linked signaling (FIG. 1). The discovery of RGS proteins and their GAP activity towards $G\alpha$ subunits resolved apparent timing paradoxes between observed rapid physiological responses mediated in vivo by GPCRs and the slow hydrolysis activity of the cognate G-proteins seen in vitro [Arshaysky et al. *Neuron,* 1998. 20(1): p. 11-4]. Thus, in this capacity as negative regulators of GPCR signal transduction, the RGS proteins present themselves as excellent potential drug discovery targets [Neubig et al. *Nat Rev Drug Discov,* 2002. 1(3): p. 187-97], given that pharmacological inhibition of RGS domain GAP activity should lead to prolonged signaling from G-proteins activated by agonist-bound GPCRs.

There are at least 37 RGS proteins encoded by the human genome that contain the signature RGS domain (reviewed in [Neubig et al. *Nat Rev Drug Discov,* 2002. 1(3): p. 187-97; Siderovski et al. *Crit Rev Biochem Mol Biol,* 1999. 34(4): p. 215-51; and Ross et al. *Annu Rev Biochem,* 2000. 69: p. 795-827]). The RGS containing proteins are listed in Table 1, along with the sequences of their respective RGS domains. These proteins are grouped according to sequence homology between their RGS domains and fall into subfamilies with similar multi-domain architectures and similar target Gα subunits. For example, the GAP activity of R7 subfamily members is specific to Gα$_{i/o}$ subunits [Hooks et al. *J Biol Chem*, 2003. 278(12): p. 10087-93], whereas that of the GEF subfamily appears specific for Gα$_{12/13}$ subunits ([Suzuki et al. *Proc Natl Acad Sci USA*, 2003. 100(2): p. 733-8; and Kozasa et al. *Science*, 1998. 280(5372): p. 2109-11]; cf. [Booden et al. *Mol Cell Biol*, 2002. 22(12): p. 4053-61]). Based on structural and biochemical studies with RGS4, RGS domains are thought to exert their GAP activity by stabilizing a conformation of Gα that favors the transition state for GTP hydrolysis [Tesmer et al. *Cell*, 1997. 89(2): p. 251-61]. Several key questions are currently being addressed in the field to validate RGS proteins as bona fide drug discovery targets, including whether RGS proteins have significant roles in vivo in the physiological timing of GPCR signal transduction. There has been focus on identifying the particular function of RGS proteins in neuronal signaling in the CNS [Neubig et al. *Nat Rev Drug Discov*, 2002. 1(3): p. 187-97].

TABLE 1

| PROTEIN NAME | ACCESSION # | RGS DOMAIN SEQUENCE |
|---|---|---|
| RGS1 | Q08116 | SLEKLLANQTGQNVFGSFLKSEFSEENIEF WLACEDYKKTESDLLPCKAEEIYKAFVHSD AAKQINIDFRTRESTAKKIKAPTPTCFDEA QKVIYTLMEKDSYPRFLKSDIYLNLL (SEQ ID NO: 21) |
| RGS2 | P41220 | AFDELLASKYGLAAFRAFLKSEFCEENIEF WLACEDFKKTKSPQKLSSKARKIYTDFIEK EAPKEINIDFQTKTLIAQNIQEATSGCFTT AQKRVYSLMENNSYPRFLESEFYQDLC (SEQ ID NO: 22) |
| RGS3 | P49796 | LEKLLVHKYGLAVFQAFLRTEFSEENLEFW LACEDFKKVKSQSKMASKAKKIFAEYIAIQ ACKEVNLDSYTREHTKDNLQSVTRGCFDLA QKRIFGLMEKDSYPRFLRSDLYLDLI (SEQ ID NO: 23) |
| RGS4 | P49798 | SLENLISHECGLAAFKAFLKSEYSEENIDF WISCEEYKKIKSPSKLSPKAKKIYNEFISV QATKEVNLDSCTREETSRNMLEPTITCFDE AQKKIFNLMEKDSYRRFLKSRFYLDLV (SEQ ID NO: 24) |
| RGS5 | O15539 | LDKLLQNNYGLASFKSFLKSEFSEENLEFW IACEDYKKIKSPAKMAEKAKQIYEEFIQTE APKEVNIDHFTKDITMKNLVEPSLSSFDMA QKRIHALMEKDSLPRFVRSEFYQELI (SEQ ID NO: 25) |
| RGS6 | P49758 | SFDEILKDQVGRDQFLRFLESEFSSENLRF WLAVQDLKKQPLQDVAKRVEEIWQEFLAPG APSAINLDSHSYEITSQNVKDGGRYTFEDA QEHIYKLMKSDSYARFLASNAYQDLL (SEQ ID NO: 26) |
| RGS7 | P49802 | GMDEALKDPVGREQFLKFLESEFSSENLRF WLAVEDLKKRPIKEVPSRVQEIWQEFLAPG APSAINLDSKSYDKTTQNVKEPGRYTFEDA QEHIYKLMKSDSYPRFIRSSAYQELL (SEQ ID NO: 27) |
| RGS8 | P57771 | SFDVLLSHKYGVAAFRAFLKTEFSEENLEF WLACEEFKKTRSTAKLVSKAHRIFEEFVDV QAPREVNIDFQTREATRKNLQEPSLTCFDQ AQGKVHSLMEKDSYPRFLRSKMYLDLL (SEQ ID NO: 28) |
| RGS9 | O75916 | NFSELIRDPKGRQSFQYFLKKEFSGENLGF WEACEDLKYGDQSKVKEKAEEIYKLFLAPG ARRWINIDGKTMDITVKGLKHPHRYVLDAA QTHIYMLMKKDSYARYLKSPIYKDML (SEQ ID NO: 29) |
| RGS10 | O43665 | SLENLLEDPEGVKRFREFLKKEFSEENVLF WLACEDFKKMQDKTQMQEKAKEIYMTFLSS KASSQVNVEGQSRLNEKILEEPHPLMFQKL QDQIFNLMKYDSYSRFLKSDLFLKHK (SEQ ID NO: 30) |
| RGS11 | O94810 | SFRELLEDPVGRAHFMDFLGKEFSGENLSF WEACEELRYGAQAQVPTLVDAVYEQFLAPG AAHWVNIDSRTMEQTLEGLRQPHRYVLDDA QLHIYMLMKKDSYPRFLKSDMYKALL (SEQ ID NO: 31) |
| RGS12 | O14924 | SFERLLQDPVGVRYFSDFLRKEFSEENILF WQACEYFNHVPAHDKKELSYRAREIFSKFL CSKATTPVNIDSQAQLADDVLRAPHPDMFK EQQLQIFNLMKFDSYTRFLKSPLYQECI (SEQ ID NO: 32) |
| RGS13 | O14921 | SFENLMATKYGPVVYAAYLKMEHSDENIQF WMACETYKKIASRWSRISRAKKLYKIYIQP QSPREINIDSSTRETIIRNIQEPTETCFEE AQKIVYMHMERDSYPRFLKSEMYQKLL (SEQ ID NO: 33) |
| RGS14 | O43566 | SFERLLQDPLGLAYFTEFLKKEFSAENVTF WKACERFQQIPASDTQQLAQEARNIYQEFL SSQALSPVNIDRQAWLGEEVLAEPRPDMFR AQQLQIFNLMKFDSYARFVKSPLYRECL (SEQ ID NO: 34) |
| RGS16 | O15492 | SFDLLLSSKNGVAAFHAFLKTEFSEENLEF WLACEEFKKIRSATKLASRAHQIFEEFICS EAPKEVNIDHETHELTRMNLQTATATCFDA AQGKTRTLMEKDSYPRFLKSPAYRDLA (SEQ ID NO: 35) |
| RGS17 | Q9UGC6 | NFDKMMKAPAGRNLFREFLRTEYSEENLLF WLACEDLKKEQNKKVIEEKARMIYEDYISI LSPKEVSLDSRVREVINRNLLDPNPHMYED AQLQIYTLMHRDSFPRFLNSQIYKSFV (SEQ ID NO: 36) |
| RGS18 | Q9NS28 | SFDKLLSHRDGLEAFTRFLKTEFSEENIEF WIACEDFKKSKGPQQIHLKAKAIYEKFIQT DAPKEVNLDFPHTKEVITNSITQPTLHSFDA AQSRVYQLMEQDSYTRFLKSDIYLDLM (SEQ ID NO: 37) |
| RGS19 | P49795 | SFDKLMHSPAGRSVFRAFLRTEYSEENMLF WLACEEELKAEANQHVVDEKARLIYEDYVSI LSPKEVSLDSRVREGINKKMQEPSAHTFDD AQLQIYTLMHRDSYPRFLSSPTYRALL (SEQ ID NO: 38) |
| RGS20 | O76081 | SFDKLMVTPAGRNAFREFLRTEFSEENMLF WMACEELKKEANKNIIEEKARIIYEDYISI LSPKEVSLDSRVREVINRNMVEPSQHIFDD AQLQIYTLMHRDSYPRFMNSAVYKDLL (SEQ ID NO: 39) |
| RGS21 | Q2M5E4 | NMDTLLANQAGLDAFRIFLKSEFSEENVEF WLACEDFKKTKNADKIASKAKMIYSEFIEA DAPKEINIDFGTRDLISKNIAEPTLKCFDE AQKLIYCLMAKDSFPRFLKSEIYKKLV (SEQ ID NO: 40) |

TABLE 1-continued

| PROTEIN NAME | ACCESSION # | RGS DOMAIN SEQUENCE |
|---|---|---|
| RGS22 | Q9BYZ4 | CEHSGNKLWKDSVYFWFDLQAYHQLFYQET LQPFKVCKQAQYLFATYVAPSATLDIGLQQ EKKKEIYMKIQPPFEDLFDTAEEYILLLLL EPWTKMVKSD (SEQ ID NO: 41) |
|  | (2 RGS domains within the RGS22 protein) | KFSDLLNNKLEFEHFRQFLETHSSSRILCA DRHWSSSGEITYRDRNQRKAKSIYIKNKYL NKKYFFGPNSPASLYQQNQVMHLSGGWGKI LHEQLDAPVLVEIQKHVQNRLENVWLPLFL ASEQF (SEQ ID NO: 42) |
| GRK1 | Q15835 | EFESVCLEQPIGKKLFQQFLQSAEKHLPAL ELWKDIEDYDTADNDLQPQKAQTILAQYLD PQAKLFCSFLDEGIVAKFKEGPVEIQDGLF QPLLQATLAHLGQAPFQEYLGSLYFLRFL (SEQ ID NO: 43) |
| GRK2 | P25098 | TFEKIFSQKLGYLLFRDFCLNHLEEARPLV EFYEEIKKYEKLETEEERVARSREIFDSYI MKELLACSHPFSKSATEHVQGHLGKKQVPP DLFQPYIEEICQNLRGDVFQKFIESDKFTR FC (SEQ ID NO: 44) |
| GRK3 | P35626 | TFDKIFNQKIGFLLFKDFCLNEINEAVPQV KFYEEIKEYEKLDNEEDRLCRSRQIYDAYI MKELLSCSHPFSKQAVEHVQSHLSKKQVTS TLFQPYIEEICESLRGDIFQKFMESDKFTR FC (SEQ ID NO: 45) |
| GRK4 | P32298 | DYSSLCDKQPIGRRLFRQFCDTKPTLKRHI EFLDAVAEYEVADDEDRSDCGLSILDRFFN DKLAAPLPEIPPDVVTECRLGLKEENPSKK AFEECTRVAHNYLRGEPFEEYQESSYFSQ FL (SEQ ID NO: 46) |
| GRK5 | P34947 | DYCSLCDKQPIGRLLFRQFCETRPGLECYI QFLDSVAEYEVTPDEKLGEKGKEIMTKYLT PKSPVFIAQVGQDLVSQTEEKLLQKPCKEL FSACAQSVHEYLRGEPFHEYLDSMFFDRFL (SEQ ID NO: 47) |
| GRK6 | P43250 | DYHSLCERQPIGRLLFREFCATRPELSRCV AFLDGVAEYEVTPDDKRKACGRQLTQNFLS HTGPDLIPEVPRQLVTNCTQRLEQGPCKDL FQEELTRLTHEYLSVAPFADYLDSIYFNRFL (SEQ ID NO: 48) |
| GRK7 | Q8WTQ7 | NEHSLCEQQPIGRRLFRDFLATVPTFRKAA TFLEDVQNWELAEEGPTKDSALQGLVATCA SAPAPGNPQPFLSQAVATKCQAATTEEERV AAVTLAKAEAMAFLQEQPPFKDFVTSAFYDK FL (SEQ ID NO: 49) |
| SNX13 | Q9Y5W8 | PLDSILVDNVALQFFMDYMQQTGGQAHLFF WMTVEGYRVTAQQQLEVLLSRQRDGKHQTN QTKGLLRAAAVGIYEQYLSEKASPRVTVDD YLVAKLADTLNHEDPTPEIFDDIQRKVYEL MLRDERFYPSFRQNALYVRML (SEQ ID NO: 50) |
| SNX14 | Q9Y5W7 | SPLVPFLQKFAEPRNKKPSVLKLELKQIRE QQDLLFRFMNFLKQEGAVHVLQFCLTVEEF NDRILRPELSNDEMLSLHEELQKIYKTYCL DESIDKIRFDPFIVEEIQRIAEGPYIDVVK LQTMRCLFEAYEHVLSLLENVFTPMFCHSD EYFRQLLRGAESP (SEQ ID NO: 51) |
| SNX25 | Q9H3E2 | QFEDILANTFYREHEGMYMERMDKRALISF WESVEHLKNANKNEIPQLVGEIYQNFFVES KEISVEKSLYKEIQQCLVGNKGIEVFYKIQ EDVYETLKDRYYPSFIVSDLYEKLL (SEQ ID NO: 52) |
| Axin | O15169 | SLHSLLDDQDGISLFRTFLKQEGCADLLDF WFACTGFRKLEPCDSNEEKRLKLARAIYRK YILDNNGIVSRQTKPATKSFIKGCIMKQLI DPAMFDQAQTEIQATMEENTYPSFLKSDIY LEYT (SEQ ID NO: 53 |
| Axin2 | Q9Y2T1 | SLHSLLGDQDGAYLFRTFLEREKCVDTLDF WFACNGFRQMNLKDTKTLRVAKAIYKRYIE NNSIVSKQLKPATKTYIRDGIKKQQIDSIM FDQAQTEIQSVMEENAYQMFLTSDIYLEYV (SEQ ID NO: 54) |
| D-AKAP2 | O43572 | TLEQVLHDTIVLPYFIQFMELRRMEHLVKF WLEAESFHSTTWSRIRAHSLNTMKQSSLAE PVSPSKKHETTASFLTDSLDKRLEDSGSAQ LFMTHSEGIDLNNRTNSTQNHLLLSQECDS AHSLRLEMARAGTHQVSMETQESSSTLTVA SRNSPASPLKELSGKLMKSIEQDAVNTFTK YISPDAAKPIPITEAMRNDIIARICGEDGQ VDP (SEQ ID NO. 55) |
|  | (2 RGS domains within the D-AKAP2 protein) | YLADILFCESALFYFSEYMEKEDAVNILQF WLAADNFQSQLAAKKGQYDGQEAQNDAMIL YDKYFSLQATHPLGFDDVVRLEIESNICRE GGPLPNCFTTPLRQAWTTMEKVFLPGFLSS NLYYKYL (SEQ ID NO: 56) |
| p115 RhoGEF | Q92888 | NSQFQSLEQVKRRPAHLMALLQHVALQFEP GPLLCCLHADMLGSLGPKEAKKAFLDFYHS FLEKTAVLRVPVPPNVAFELDRTRADLISE DVQRREVQEVVQSQQVAVGRQLEDFRSKRL MGMTPWEQELAQLEAWVGRDRASYEAREHR VAERLLMHLEEMQHTISTDEEKSAAVVNAI GLYMRHLGVRTKSGDKKSGRNFFRKKVMGN (SEQ ID NO: 57) |
| PDZ RhoGEF | O15085 | DLEKLKSRPAHLGVFLRYIFSQADPSPLLF YLCAEVYQQASPKDSRSLGKDIWNIFLEKN APLRVKIPEMLQAEIDSRLRNSEDARGVLC EAQEAAMPEIQEQIHDYRTKRTLGLGSLYG (SEQ ID NO: 58) |
| LARG | Q9NZN5 | CSCFQSIELLKSRPAHLAVFLHHVVSQFDP ATLLCYLYSDLYKHTNSKETRRIFLEFHQF FLDRSAHLKVSVPDEMSADLEKRRPELIPE DLHRHYIQTMQERVHPEVQRHLEDFRQKRS MGLTLAESELTKLDAERDKDRLTLEKERTC AEQIVAKIEEVLMTAQAVEEDKSSTMQYVI LMYMKHLGVKVKEPRNLEHKRGIGFLPKI (SEQ ID NO: 59) |

A link between pharmacological modulators of RGS functionality and signal transduction through GPCR activity could result in a drug with important clinical significance, particularly in the field of neurological disorders. It seems likely that pharmacological interventions for many neurological disorders would involve a combination of effects. Such effects may include an agonist to induce a response mediated by a GPCR complex and an inhibitor of RGS activity to prolong the effect seen with the initial agonist. However, efforts to screen compound libraries for inhibitors or activators of RGS proteins have been hampered because the GTPase activity of isolated Gα proteins is limited by GDP dissociation, so steady state GTPase activity cannot be used to measure GAP activity.

RGS proteins accelerate the rate of Gα-catalyzed GTP hydrolysis by as much as 100-fold, which provides the basis for an in vitro screening assay; moreover both types of proteins are soluble and relatively easy to produce. However, in the absence of GPCR-mediated nucleotide exchange, it is GDP release (rather than GTP hydrolysis) that is the rate-limiting step in the Gα nucleotide cycle. Thus, to examine the effect of an RGS protein in accelerating GTP hydrolysis by an isolated Gα subunit in vitro, a single round of hydrolysis of radiolabelled GTP is usually performed (a.k.a. the "single-turnover GTPase assay"). This standard assay for measuring RGS domain-mediated GAP activity is low-throughput and requires discrete steps of [γ-$^{32}$P]GTP loading onto Gα, purification of the [γ-$^{32}$P]GTP-Gα complex, and its immediate use before significant hydrolysis by intrinsic $G_\alpha$ GTPase can occur. The assay also involves isolation (in discrete time intervals) of released [$^{32}$P]phosphate with activated charcoal precipitation and centrifugation, and finally scintillation counting. This type of protocol would be very difficult to incorporate into an automated high through put screening (HTS) environment. Moreover, measurement of steady state enzyme activity is the standard approach used for both basic research and HTS; all of the assumptions of Michaelis-Menten kinetic analysis are based on steady state measurements. Use of a single turnover assay thus adds additional complications in data analysis.

Reliance on reconstituted GPCR/G protein complexes and phosphate detection make steady state Gα GTPase methods unsuitable for HTS. Steady-state GTPase measurements of RGS protein GAP activity are carried out in the presence of an agonist-activated GPCR/heterotrimer complex to effect the exchange of GTP for bound GDP (see FIG. 2). This entails the use of native or heterologously co-expressed GPCRs and Gβγ proteins within membrane preparations from mammalian or Sf9 insect cells, or elaborate reconstitution of purified receptor and heterotrimer in lipid vesicles. [γ-$^{32}$P]GTP radioassays utilizing charcoal to adsorb unhydrolyzed [γ-$^{32}$P]GTP are generally used as a detection method, similar to the single turnover assays. The complexity and expense of using reconstituted GPCRs combined with the regulatory and disposal costs for radioactive waste limits the utility of these assay methods for an industrial HTS environment. Alternatives to radioassays have been developed that rely on colorimetric or fluorescent phosphate detection methods, however the high background levels of phosphate in biological reagents impose stringent requirements on their use. Moreover, the intent in a biochemical HTS assay is to identify inhibitors of a specific molecular target. The difficulty of deconvoluting hits from such a complex assay make it very unattractive; one might as well use a cellular assay, where the potential for interaction with multiple targets—including the GPCR itself—is not generally perceived as a disadvantage.

The present invention enables the use of biochemical assay methods to screen for modulators of RGS GAP catalytic activity. Altering the relative rates of Gα protein GTPase and GDP dissociation through mutation, so that GDP dissociation is no longer rate limiting, allows the use of steady state enzymatic assays for monitoring changes in Gα GTPase activity. As background, there is literature relating to single amino acid substitutions of important functional residues, which are highly conserved within all Gα proteins subfamilies. These mutations are identified below.

Single Mutation of a Conserved Arginine:

There are two examples of mutant Gα proteins from different subfamilies where GTP hydrolysis has been reduced more than 100-fold without disrupting RGS interactions. Native G$\alpha_{i1}$ and G$\alpha_q$ have similar basal GTP hydrolysis rates (single turnover; Table 3.) of 3.0 min$^{-1}$ and 0.7 min$^{-1}$, respectively [Krumins et al. *Methods Enzymol*, 2002. 344: p. 673-85]. Mutation of a highly conserved active site Arg residue in either protein (R178C and R183C, respectively, for G$\alpha_{i1}$ and G$\alpha_q$) causes an approximate 100-fold reduction in GTPase turnover rate, but it does not abolish their functional interaction with RGS proteins. RGS4 stimulates the GTPase activity of both mutant proteins approximately 100-fold [Berman et al. *Cell*, 1996. 86(3): p. 445-5; and Chidiac et al. *J Biol Chem*, 1999. 274(28): p. 19639-43]—a factor equal to or greater than its GAP effect on the wild type protein. In the case of the G$\alpha_q$ R183C protein, functional interaction (i.e., stimulation of GTPase) has been demonstrated with several additional RGS proteins including RGS1, RGS2, RGS3, RGS-GAIP and with phospholipase C$\beta_1$ [Chidiac et al. *Methods Enzymol*, 2002. 344: p. 686-702]. Mutation or covalent modification of the cognate Arg in three additional $G_\alpha$ proteins, G$\alpha_{i2}$, G$\alpha_s$ and G$\alpha_t$, causes similar losses of GTP hydrolysis activity [Berman et al. *Cell*, 1996. 86(3): p. 445-5; Freissmuth et al. *J Biol Chem*, 1989. 264(36): p. 21907-14; and Nishina et al. *J Biochem* (Tokyo), 1995. 118(5): p. 1083-9], though their interaction with RGS proteins has not yet been examined. The 20 Gα family members (i.e., reference native Gα proteins) and the locations of the critical Arginine and Alanine amino acids are presented in Table 2.

TABLE 2

| SEQ ID NO: | Gα Family Member | GenBank Accession # | Conserved Arg Amino Acid # | Conserved Ala Amino Acid # |
|---|---|---|---|---|
| 1 | i1 | P63096 | 178 | 326 |
| 2 | i2 | NP_002061 | 179 | 327 |
| 3 | i3 | AAM12621 | 178 | 326 |
| 4 | 12 | NP_031379 | 205 | 353 |
| 5 | 13 | NP_006563 | 200 | 349 |
| 6 | q | NP_002063 | 183 | 331 |
| 7 | s | P63092 | 201 | 366 |
| 8 | z | NP_002064 | 178 | 327 |
| 9 | i/o | NP_620073 | 179 | 326 |
| 10 | q11 | NP_002058 | 183 | 331 |
| 11 | q15 | NP_002059 | 186 | 346 |
| 12 | 14 | AAH27886 | 179 | 327 |
| 13 | O | NP_066268 | 179 | 326 |
| 14 | oB | AAM12609 | 179 | 326 |
| 15 | oA | AAM12608 | 179 | 326 |
| 16 | olf | AAM12607 | 188 | 353 |
| 17 | k | AAA35896 | 178 | 326 |
| 18 | s2 | AAA53147 | 202 | 367 |
| 19 | s3 | AAA53148 | 186 | 351 |
| 20 | s4 | AAA53149 | 187 | 352 |

The effects of catalytic site Arg mutations on Gα GTPase activity, GDP dissociation and RGS interactions are described in Table 3.

TABLE 3

| Gα Protein | WT $k_{cat\,GTPase}$ | WT $k_{off\,GDP}$ | Arg Mutant $k_{cat\,GTPase}$ | Arg Mutant $k_{off\,GDP}$ | RGS Interactions |
|---|---|---|---|---|---|
| G$\alpha_{i1}$ | 3.0 | 0.087 | R178C 0.02-0.04 | >0.087 | RGS4 |
| G$\alpha_{i2}$ | 4.0 | 0.02-0.04 | R179C 0.01-0.05 | 0.01-0.04 | NA |

TABLE 3-continued

| Gα Protein | WT $k_{cat\ GTPase}$ | WT $k_{off\ GDP}$ | Arg Mutant $k_{cat\ GTPase}$ | Arg Mutant $k_{off\ GDP}$ | RGS Interactions |
|---|---|---|---|---|---|
| Gα$_q$ | 0.7* | NA | R183C 0.005 | NA | RGS1, 2, 3, 4, GAIP, PLCβ1 |
| Gα$_{s4}$ | 3.8 | 0.14 | R187A 0.03 | 0.27 min$^{-1}$ | NA |

All rates are per minute. All $k_{cat}$ values were determined using single turnover GTP hydrolysis assays with isolated Gα proteins except WT G$_{αq}$ kcat, which was determined in reconstituted GPCR/Gβγ system.
Data from [Posner et al., 1998] and [Coleman et al. *Science*, 1994. 265(5177): p. 1405-12] (Gα$_{i1}$), [Nishina et al., 1995] (Gα$_{i2}$), [Chidiac et al., 1999] (Gα$_q$) and [Freissmuth et al., 1989] (Gα$_{s4}$).
NA = Not Available.

Single Mutation of a Conserved Alanine:

There are also several examples of Gα mutations that increase GDP dissociation without affecting GTP hydrolysis. The most striking is the A326S mutant of Gα$_{i1}$, which exhibits a 25-fold increase in $k_{off(GDP)}$ relative to wildtype protein and an identical $k_{cat\ GTP}$ [Posner et al. *J Biol Chem*, 1998. 273(34): p. 21752-8]. Moreover, RGS4 stimulated the steady state GTPase activity of Gα$_{i1}$ A3265 appreciably, from 1.3 min$^{-1}$ to 2.2 min$^{-1}$. Thus, an additional mutation that caused a relatively small decrease in $k_{cat\ GTPase}$ for the Gα$_{i1}$ A326S mutant would produce a $k_{off(GDP)}/k_{cat(GTPase)}$ of five or more, enabling detection of RGS GAP activity with good signal-to-noise.

Efforts to produce mutant Gα proteins have yielded proteins with decreases in their rates of GTP hydrolysis or increases in GDP dissociation from Gα proteins. Neither of these strategies have facilitated a useful system for compound library screening, where the dissociation of GDP is no longer rate limiting. Applicants envision that the ability to possibly achieve such an increase in GDP dissociation relative to GTP hydrolysis is highly likely to enable detection of RGS protein GAP activity using steady state GTPase assays. Accordingly, having the tools to examine drug interactions on RGS proteins would result in a significant improvement to the currently existing technology and potentially to important drug discoveries for the treatment of a wide variety of human disorders.

BRIEF SUMMARY OF THE INVENTION

The present invention is summarized as genetically engineered G-alpha proteins. These proteins are components of the G-protein-coupled receptor (GPCR) signal transduction pathway. The engineered protein is a mutant Gα protein, which in some examples contains alterations of at least one, and preferably two or more, highly conserved amino acid residues, which are conserved among all four subfamilies of Gα proteins, and among all specific members of families investigated. The mutations described here yield an unexpectedly high effect on Gα function both in terms of GTPase activity (GTP hydrolysis) and GDP recycling. This effect is more than additive when considered in light of the individual mutations. This unanticipated synergistic effect may have a profound influence on the way GPCR signaling pathways are examined for the development of new pharmacotherapies, particularly in the field of central nervous system disorders such as Parkinson's disease.

In one aspect, the invention includes an engineered protein including a Gα protein differing in amino acid sequence from a reference native Gα protein, wherein the difference includes at least two amino acid substitutions, wherein the substitutions have a net effect of an increase in the GDP dissociation rate and a decrease in the GTP hydrolysis rate, so that the rate of GDP dissociation is no longer rate limiting for catalysis relative to a Gα protein without said amino acid substitutions. In a related aspect, the reference Gα protein includes an amino acid sequence from any one of SEQ ID NOs: 1-20.

In another aspect, the invention includes kit having at least one engineered Gα protein described herein.

In another aspect, the invention includes an engineered Gα protein described herein, wherein when the engineered Gα protein is in the presence of an RGS protein, the detectable steady state GTPase activity is increased at least two-fold relative to the GTPase activity of Gα protein in the absence of an RGS protein.

In another aspect, the invention includes an engineered Gα protein differing in amino acid sequence from a reference native Gα protein, wherein the difference consists of two amino acid substitutions, wherein the first substitution is at (i) the conserved Arginine located in the native Gα protein at any one of amino acid positions ranging from about 178 to about 205, and the second substitution is at (ii) the conserved Alanine located in the native Gα protein at any one of amino acid positions ranging from about 326 and about 367, wherein both substitution result in a net effect of an increase in the GDP dissociation rate and a decrease in the GTP hydrolysis rate, so that the rate of GDP dissociation is no longer rate limiting for catalysis relative to a Gα protein without said amino acid substitutions.

In a related aspect, the invention includes an engineered Gα protein described herein having a protein differing in amino acid sequence from a reference Gα protein of any one of SEQ ID NOs: 1-20, wherein the difference consists of substituting (i) an Arginine, located at positions ranging from about 178 to about 205, to any one of Methionine, Cysteine or Lysine, and (ii) an Alanine, located at positions ranging from about 326 to about 367, to any one of Serine, Threonine or Aspartate.

In a related aspect, the invention includes the engineered Gα protein described herein having a protein differing in amino acid sequence from a reference Gα protein of any one of SEQ ID NOs: 1-20, wherein the difference consists of an Arginine to a Methionine substitution located at positions ranging from about 178 to about 205, and an Alanine to a Serine substitution located at positions ranging from about 326 to about 367, wherein when the engineered Gα protein is in the presence of an RGS protein, the detectable steady state GTPase activity is increased at least two-fold relative to the GTPase activity of Gα protein in the absence of an RGS protein.

In another aspect, the invention includes a method of using the engineered Gα protein of Claim 1, wherein the method includes incubating the engineered Gα protein in the presence or absence of a protein containing an RGS domain.

In a related aspect, the invention includes a method of using an engineered Gα protein, wherein the method includes incubating the engineered Gα protein in the presence or absence of a protein containing an RGS domain, wherein the engineered Gα protein differs in amino acid sequence from a reference native Gα protein in at least two amino acid substitutions, wherein the substitutions have a net effect of an increase in the GDP dissociation rate and a decrease in the GTP hydrolysis rate, so that the rate of GDP dissociation is no longer rate limiting for catalysis relative to a Gα protein without said amino acid substitutions.

In a related method, the invention further includes determining GAP activity, wherein when the engineered Gα protein is incubated in the presence of a protein containing an RGS domain, the Gα GTPase activity is stimulated, which is a measure of its GAP activity.

In a related aspect, the invention includes a method of detecting the enzymatic GAP activity of an RGS protein by using an engineered Gα protein of Claim 1 in the method including the steps of: a) reacting the engineered Gα protein with guanosine triphosphate (GTP) in the presence and absence of another protein containing an RGS domain; b) forming the products guanosine diphosphate (GDP) and phosphate; c) detecting the GDP or phosphate as a measure of Gα GTPase activity; and d) determining the GAP activity by subtracting the GTPase activity in the absence of the protein containing an RGS domain from the GTPase activity in the presence of the protein containing an RGS domain.

In a related aspect, the invention includes method of detecting the enzymatic GAP activity of an RGS protein by using an engineered Gα protein variant of Claim 1 with the method including the steps of: a) reacting the engineered Gα protein with guanosine triphosphate (GTP) in the presence and absence of another protein containing an RGS domain; b) forming the products guanosine diphosphate (GDP) and phosphate; c) contacting the GDP produced in this reaction with a first complex including an antibody being specific for the GDP and a fluorescent tracer, and capable of producing an observable; d) competitively displacing the tracer of the first complex by the GDP, to generate a second complex GDP-antibody complex and displaced tracer, to directly detect the GDP in the reaction; and e) determining the GAP activity by subtracting the GDP formation in the absence of the protein containing an RGS domain from the GDP formation in the presence of the protein containing an RGS domain.

Other advantages and a fuller appreciation of specific adaptations, compositional variations, and physical attributes will be gained upon an examination of the following detailed description of the various embodiments, taken in conjunction with the appended claims.

BRIEF DESCRIPTION OF THE SEVERAL VIEWS OF THE DRAWINGS

Figure 3A:
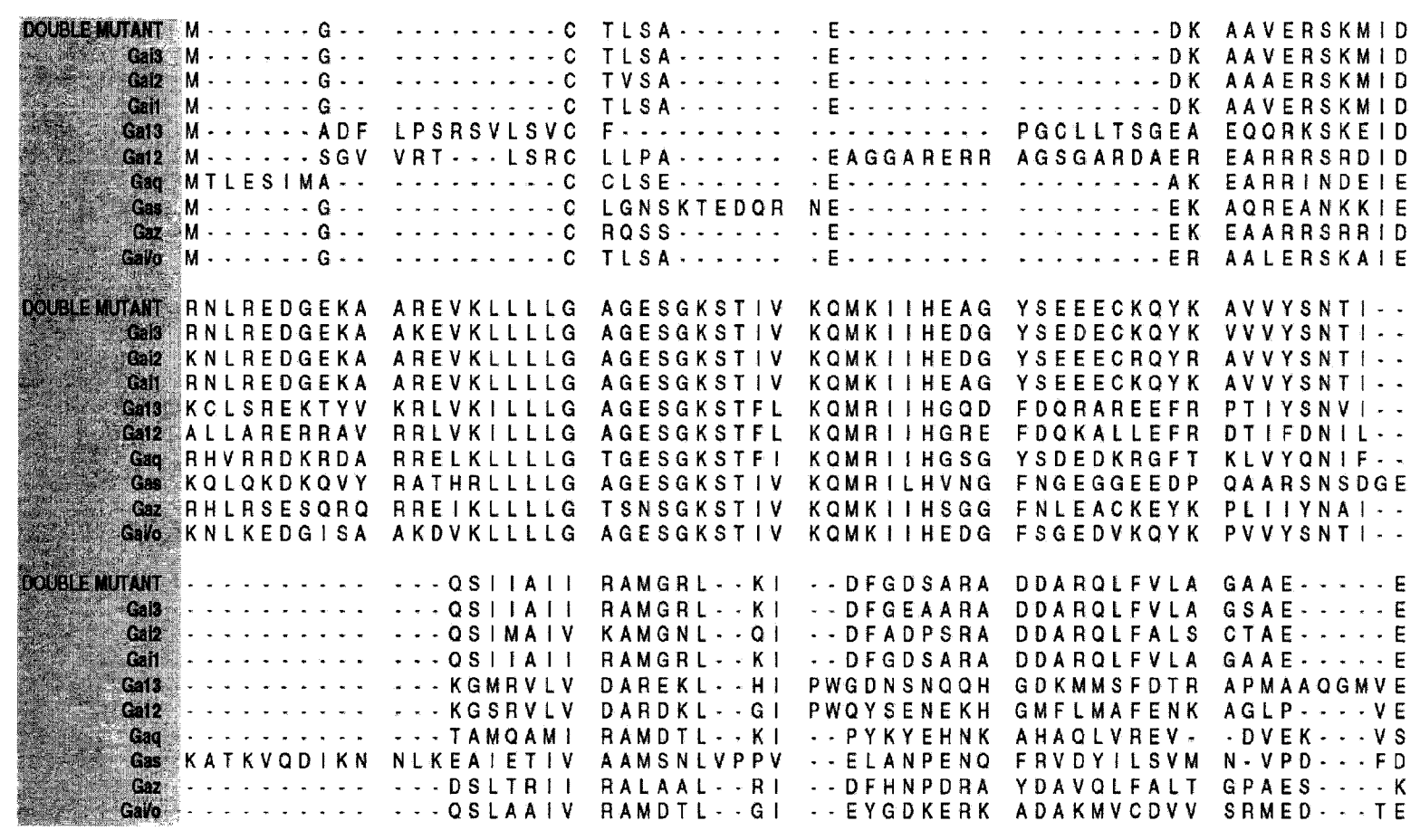
Figure 3B:
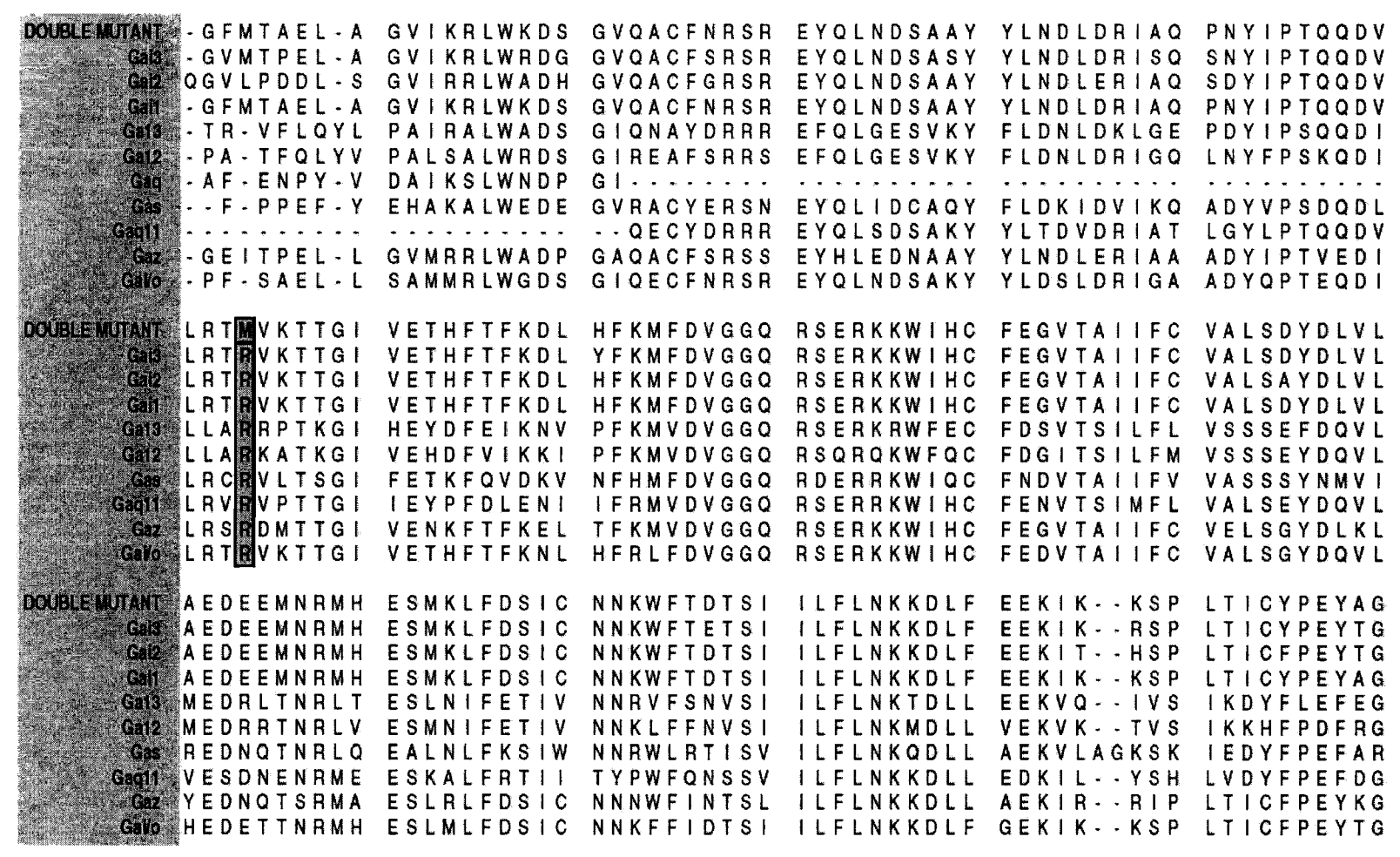

FIG. 3 provides a sequence alignment for some members of the human Gα protein family, including all 4 subfamilies; $Gα_i$ (members 1, 2, 3, z, and i/o; SEQ ID NOs: 1, 2, 3, 8, and 9 respectively), $Gα_q$ (members q and 11; SEQ ID NOs: 6 and 10 respectively), $Gα_{12\ \&\ 13}$ (SEQ ID NOs: 4 and 5 respectively), and $Gα_s$ (SEQ ID NO: 7). Also shown is the described invention, a $Gα_{i1}$ double mutant (SEQ ID NO: 60), which demonstrates the changes conferred upon the conserved residues of interest (R178 and A326).

FIG. 4 shows the polynucleotide sequence (SEQ ID NO: 61) and the amino acid sequence (SEQ ID NO: 1) for the human guanine nucleotide binding protein alpha i1 (GNAI1). All mutants described in FIG. 4 were derived from this reference sequence, GenBank Accession # AF493905 and P63096.

Figure 1:
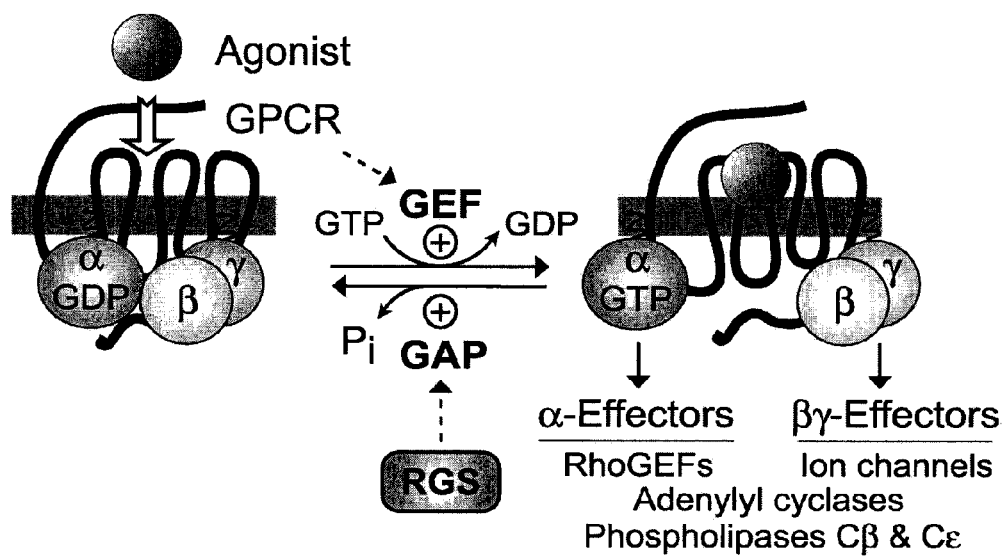
FIG. 1 illustrates a model of the G-protein signaling complex, which is described in this invention. Agonist activation of the GPCR results in conformational changes transmitted to the Gαβγ heterotrimer resulting in the release of GDP from Gα and subsequent exchange for GTP (thus serving as guanine nucleotide exchange factors or GEFs), release of Gβγ, and signal commencement [Hamm, H. E. *Proc Natl Acad Sci USA*, 2001. 98(9): p. 4819-21]. Activated Gα·GTP and liberated Gβγ modulate the activity of several downstream effectors responsible for cellular responses to extracellular ligands. RGS proteins facilitate signal termination by increasing the intrinsic GTP hydrolysis rate of Ga·GTP, thus serving as GTPase-accelerating proteins (GAPs).

Before the various embodiments of the invention are explained in detail, it is to be understood that the invention is not limited in its application to the details set forth in the following description. The invention is capable of being practiced or being carried out in a variety of ways. Also, it is to be understood that the phraseology and terminology used herein is for the purpose of description and should not be regarded as limiting in any way.

DETAILED DESCRIPTION OF THE INVENTION

The present invention is directed to novel and non-obvious genetically engineered G-alpha proteins. These proteins have been engineered in a novel way to contain at least one or more mutations, which result in a greater than additive effect than the single mutations alone. This synergistic effect was greater than that expected from previous work.

The $k_{off\ (GDP)}/k_{cat\ (GTPase)}$ for wildtype $Gα_{i1}$ is 0.03. By introducing mutations that affect $k_{off\ (GDP)}$ and $k_{cat\ (GTPase)}$, inventors hoped to achieve a ratio of at least five, a 150-fold increase. This would allow detection of a five-fold enhancement of steady state GTPase activity by RGS proteins, which inventors believe provides adequate signal-to-noise ratio for an HTS assay. (Note that it is not necessary to detect the full potential GAP activity of an RGS protein in an assay for identifying inhibitors.)

This approach was acknowledged to be of high risk because it required Gαproteins with GDP dissociation rates that are not just equal, but significantly greater than their GTP hydrolysis rates—a reversal of the natural situation. Mutations of $Gα_{i1}$ or other closely related Gα proteins that affect either (but not both) $k_{off(GDP)}$ and $D_{cat\ (GTPase)}$ without affecting functional interaction with RGS proteins have been previously identified and are set forth in Table 4 below. The most striking of these were mutations of a highly conserved active site Arg R178C, which causes an approximate 100-fold reduction in $Gα_{i1}$ GTPase turnover rate, and A326S which results in a 25-fold increase in $k_{off\ (GDP)}$ relative to wildtype protein and an identical $k_{cat\ GTP}$ [Posner et al. *J Biol Chem*, 1998. 273(34): p. 21752-8]. The novel approach described in this invention was to combine mutations to yield a synergistic effect of these separate inventions to yield a mutant Gα protein with a profoundly lower $k_{cat\ (GTPase)}$ and a profoundly higher $k_{off(GDP)}$.

Previously reported mutations that were used to develop strategy for altering $Gα_{i1}$ GTP hydrolysis and GDP dissociation rates are identified below in Table 4.

TABLE 4

| Mutation | Gα protein mutated | Decrease in $k_{cat\,(GTPase)}$ | Increase in $k_{off\,(GDP)}$ | Equivalent Site in Gα$_{i1}$ | RGS Interactions (with mutant) |
|---|---|---|---|---|---|
| A326S [Posner et al., 1998] | Gα$_{i1}$ | none | 25x | A326 | RGS4 |
| D55G/G56S [Mello et al., J Protein Chem, 2002. 21(1): p. 29-34] | Gα$_t$ | none | 10x | A50/G60 | NA |
| R144A [Remmers et al., Biochemistry, 1999. 38(42): p. 13795-800] | Gα$_{i1}$ | ND | 5x | R144 | NA |
| R178C [Coleman et al., 1994] | Gα$_{i1}$ | >100x | Reported, not quantified | R178 | RGS4 |
| T182A [Nishina et al., 1995] | Gα$_{i2}$ | >100x | 2x | T181 | NA |

Accordingly, the present invention will now be described in detail with respect to such endeavors; however, those skilled in the art will appreciate that such a description of the invention is meant to be exemplary only and should not be viewed as being limiting on the full scope thereof.

All technical and scientific terms used herein have the same meaning as is commonly understood by one of ordinary skill in the relevant art.

DEFINITIONS

"Amino acid" embraces all compounds (natural and synthetic) including both amino functionality and acid functionality, including amino acid analogs and derivatives. The instant amino acids may be those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan. "Amino acid sequence" and terms such as "polypeptide" or "protein" are not meant to limit the amino acid sequence to the complete, native amino acid sequence associated with the recited protein molecule.

"G-alpha protein" or "Gα protein" refers to the first described of three subunits which together comprise the receptor component of GPCR (G-Protein Coupled Receptor) essential to this important signal transduction system (see FIG. 1). The G-alpha subunit is responsible for nucleotide binding. An agonist induces a conformation changes in the GPCR complex which enhances the nucleotide-exchange activity of the receptor, which leads to the release of GDP and subsequent binding of GTP. Throughout this application inventors use Gα to refer in general to the alpha subunit of the Gαβγ heterotrimer. There are twenty Gα proteins classified in four subfamilies, which inventors denote by Gs, Gi, G$_{12}$, and Gq. The individual isoforms of the Gi subfamily are Gα$_{i1}$, Gα$_{i2}$, Gα$_{i3}$, and Gα$_{i/o}$. These proteins have been isolated, sequenced and characterized. The twenty known Gα protein family members are homologues and possess substantial sequence similarity. The G alpha proteins are listed with GenBank Accession numbers in Table 2.

"Engineered G-alpha protein" includes at least one or a limited number of amino acid substitutions (e.g., conservative or non-conservative substitutions), additions, or deletions (e.g., truncations) compared to wild type protein. The present invention further encompasses engineered G-alpha variants that have at least two amino acid substitutions at positions that are functionally equivalent to positions 178 and 326 of the human G alpha i1 protein (SEQ ID NO: 1) and which result in the desired function. In one aspect, such substitutions have a net effect of an increase in the GDP dissociation rate and a decrease in the GTP hydrolysis rate, such that the rate of GDP dissociation is no longer rate limiting for catalysis relative to a Gα protein without the amino acid substitutions. Suitable regions for amino acid substitutions include an Arginine to a Methionine, Cysteine or Lysine substitution from positions 178 to 205, and an Alanine to a Serine, Threonine or Aspartate substitution from positions 326 and 367 of native Gα proteins described here in Table 2.

"RGS protein" refers to multifunctional GTPase-accelerating proteins that contain a ~120 amino acid RGS sequence domain and inactivate G-protein signaling pathways. GTPase-accelerating protein activity is a general feature of RGS proteins and serves to facilitate the inactivation of the G protein rather than the receptor. Thus, agents that bind and inhibit RGS proteins could modulate endogenous neurotransmitter and hormone signaling in a manner analogous to neurotransmitter uptake inhibitors. The thirty-seven known RGS proteins are listed with GenBank Accession numbers and RGS domain sequences in Table 1. Functionally equivalent fragments of RGS proteins and fragments thereof are also included in the methods of this invention.

"GPCR" refers to G-Protein Coupled Receptor signal transduction three component systems. GPCRs are composed of a receptor, a G protein and an effector component.

"G-protein inhibitors" refers to any agent or set of agents that interferes with G-protein function either directly or indirectly. These inhibitors may act competitively or in an allosteric fashion and may act directly through RGS binding. Such an inhibitor may affect the GTPase activity, the nucleotide exchange activity of the G-protein or both.

"Allosteric" means regulation of G-protein activity by binding of an effector molecule at a site other than the GTP binding site or the site of interaction with an RGS protein.

"Homologous," "homolog" or "homologue" means amino acid sequences that share at least 30-40%, 40-50%, 50-60%, 60-70%, 70-80%, 80-90% or 95+% homology and a common functional activity.

"Conservative amino acid substitutions" means substitutions predicted to least interfere with the properties of the original protein, i.e., the structure and especially the function of the protein is conserved and not significantly changed by such substitutions. Conservative amino acid substitutions generally maintain (a) the structure of the polypeptide backbone in the area of the substitution, (b) the charge or hydrophobicity of the molecule at the site of the substitution, and/or (c) the bulk of the side chain. The invention encompasses substitution of amino acids based upon the probability of an amino acid substitution resulting in conservation of function.

"Conserved sequence" means similar or identical sequences of nucleic acids or amino acids to multiple other species of organisms, or to different molecules produced by the same organism.

"Substantial sequence similarity" in the amino acid sequence comparison context means either that the segments (or, their complementary strands) when compared, are identical when optimally aligned with appropriate amino acid insertions, deletions or substitutions in at least about 50% of the amino acids, at least 56%, at least 59%, at least 62%, at least 65%, at least 68%, at least 71%, at least 74%, at least 77%, at least 80%, at least about 85%, at least about 90%, at least about 95 to 98%, or, as high at about 99% or more of the amino acids.

"Wild-type protein" may be produced by synthetic methods. Wild-type proteins include, but are not limited to, forms that include post-translational modifications such as glycosylation as well as any preprocessed forms. In contrast, the terms "modified", "mutant", and "variant" refer to a gene or gene product that displays modifications in sequence when compared to the wild-type gene or gene product. It is noted that naturally-occurring mutants can be isolated; these are identified by the fact that they have altered nucleic acid or polypeptide sequence when compared to the wild-type gene or gene product. This is in contrast to synthetic mutants that are changes made in a sequence through human (or machine) intervention.

"Fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions with its various ligands and/or substrates. In some embodiments, fragments (e.g., G-alpha protein or RGS protein) possess an activity of the native protein or a functionally equivalent activity of the native protein.

"Kit" refers to any delivery system for delivering materials. In the context of reaction materials (e.g., compositions comprising at least one G-alpha protein described herein). Such delivery systems include systems that allow for the storage, transport, or delivery of reaction reagents and/or supporting materials (e.g., written instructions for using the materials, etc.) from one location to another. For example, kits include one or more enclosures (e.g., boxes) containing the relevant reaction reagents and/or supporting materials. Also encompassed here is a "fragmented kit" which refers to delivery systems comprising two or more separate containers that each contain a subportion of the total kit components. The containers may be delivered to the intended recipient together or separately. For example, a first container may contain a composition comprising at least one G-alpha protein described herein for a particular use, while a second container contains a second agent. Indeed, any delivery system comprising two or more separate containers that each contains a subportion of the total kit components are included in the term "fragmented kit." In contrast, a "combined kit" refers to a delivery system containing all of the components of a reaction materials needed for a particular use in a single container (e.g., in a single box housing each of the desired components). The term "kit" includes both fragmented and combined kits.

Methods and Materials

Molecular Biology and Protein Production Methods.

Full length human $G\alpha_{i1}$ and mutants were made from a pProEX HTb-$G\alpha_{i1}$ vector using a Stratagene QuikChange® II Site-Directed Mutagenesis Kit. Mutagenesis primers were designed using Stratagene's QuikChange® primer design program and were synthesized and PAGE purified by Sigma-Genosys. All sequencing primers were purchased from Sigma-Genosys. All constructs were sequence verified at Functional Biosciences LLC, Madison Wis. His-tagged wild type and mutant $G\alpha_{i1}$ proteins and human His-tagged RGS4 (23-298) were expressed in Rosetta2 (DES) cells. 250 ml cultures were grown at 37° C. to an $A_{600}$ of approximately 0.8 and then induced with 1 mM isopropyl-β-D-thiogalactopyranoside for 4 h at 25° C. All proteins were purified using a Qiagen QIAexpress® Ni-NTA Fast Start Kit following the protocol for purification of 6×His-tagged proteins under native conditions. Purified proteins were analyzed on SDS-PAGE and determined to be >95% purity. Protein concentrations were determined using a standard Bradford protein determination assay with BSA as standard. Purified proteins were stored at −20° C. in 20 mM Tris pH 7.5, 200 mM NaCl, 1 mM DTT, 5% Glycerol and 1 uM GDP for $G\alpha_{i1}$ proteins, and the same storage buffer without GDP for RGS4.

Inventors chose $G\alpha_{i1}$ as the native Gα protein background for this invention because: (a) the previous single mutations of R178C and A326S had been shown to exhibit significantly decreased $k_{cat\ (GTPase)}$ and increased $k_{off\ (GDP)}$, respectively, and to functionally interact with RGS proteins, (b) the wild-type protein interacts with a variety of RGS proteins [Krumins et al. *Methods Enzymol*, 2002. 344: p. 673-85], and (c) the wild type protein and the R178C and A326S mutants are easily expressed in *E. coli*, and the purified proteins are stable.

Combining Active Site and GDP Dissociation Mutations Enables Detection of RGS GAP Activity.

Based on the previous single mutation studies, inventors constructed 18 variants of $G\alpha_{i1}$ with the mutations shown in Table 5. Note that multiple substitutions were made at most sites, including amino acids that were intended to be more or less disruptive than the original reported mutation. For instance, R178K was tested as a conservative substitution at the catalytic arginine, and R178M was intermediate relative to the original R178C variant; it was thought that either of these alternative substitutions might result in a smaller decrease in $k_{cat\ (GTPase)}$ than R178C.

TABLE 5

| | Gαi1 variants |
|---|---|
| | Protein |
| | Gαi1 wild type |
| 1 | Gαi1 A326D |
| 2 | Gαi1 A326T |
| 3 | Gαi1 A326S |
| 4 | Gαi1 R178C |
| 5 | Gαi1 T181V |
| 6 | Gαi1 T181S |
| 7 | Gαi1 T181A |
| 8 | Gαi1 R178M |
| 9 | Gαi1 R178K |
| 10 | Gαi1 F336A |
| 11 | Gαi1 K192A |
| 12 | Gαi1 K192A F336A |

TABLE 5-continued

Gαi1 variants

| | Protein |
|---|---|
| 13 | Gαi1 R178C A326S |
| 14 | Gαi1 T181A A326S |
| 15 | Gαi1 A326S D26G G27S |
| 16 | Gαi1 R178M/A326S |
| 17 | Gαi1 R178M/A326T |
| 18 | Gαi1 R178C/A326S |

EXAMPLES

Inventors have developed a biochemical assay to screen for modulators of RGS GAP catalytic activity. There are two key components to our approach: (1) altering the relative rates of Gα GTPase and GDP dissociation so that GDP dissociation is no longer rate limiting will allow the use of steady state enzymatic assays for monitoring changes in Gα GTPase activity, and (2) selective immunodetection of GDP will enable homogenous, fluorescence-based detection of Gα GTPase activity in a multiwell format. In combination, these developments will enable direct detection of RGS-catalyzed stimulation of Gα GTP hydrolysis in a robust HTS format.

Inventors have produced a novel double mutant of the $G\alpha_{i1}$ protein to overcome the disparity between GDP dissociation and GTPase activity. Both parameters can be significantly altered by mutation without affecting functional interaction of $G\alpha_{i1}$ with RGS proteins [Berman et al. *Cell*, 1996. 86(3): p. 445-52; and Posner et al. *J Biol Chem*, 1998. 273(34): p. 21752-8]. Moreover, other Gα proteins have been shown to be similarly affected by mutation of cognate amino acids [Chidiac et al. *J Biol Chem*, 1999. 274(28): p. 19639-43; and Iiri et al. *Nature*, 1994. 371(6493): p. 164-8], so the use of mutant Gα proteins for steady state GTPase assays is potentially a generic approach.

Example 1

Testing of the Novel Gαi1 Mutants for GDP Dissociation and GTP Hydrolysis Rates

Figure 2A:
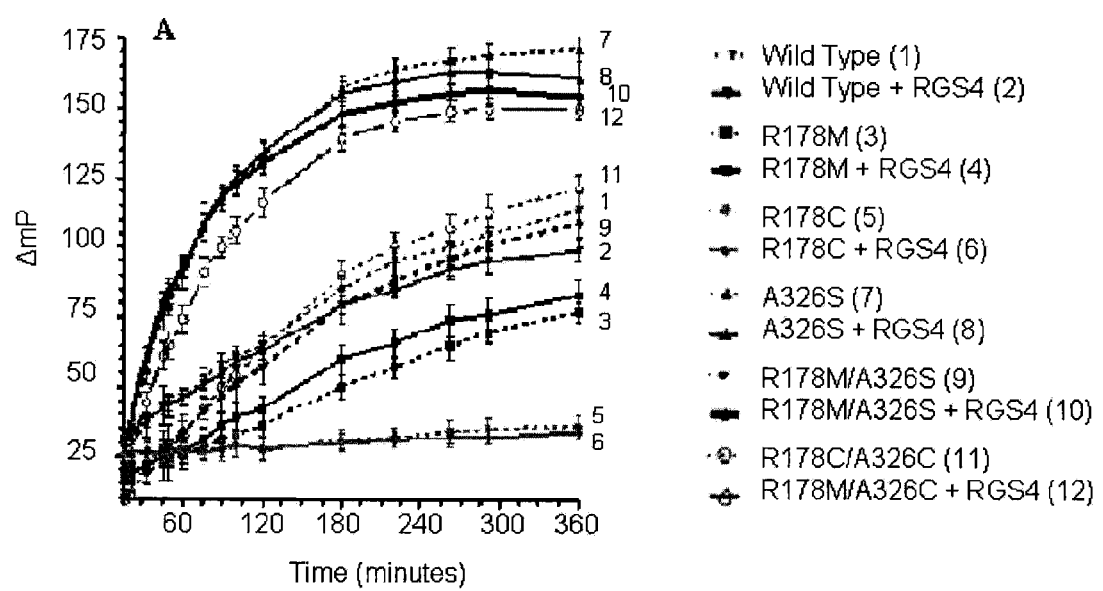
FIG. 2 shows the effect of RGS4 on steady state GTPase activity of wild type (WT) and mutated Giα1 proteins shown as: (A) change in polarization, and (B) GDP produced. Dashed lines are in the absence and solid lines are in the presence of 250 nM RGS4.
Figure 2B:
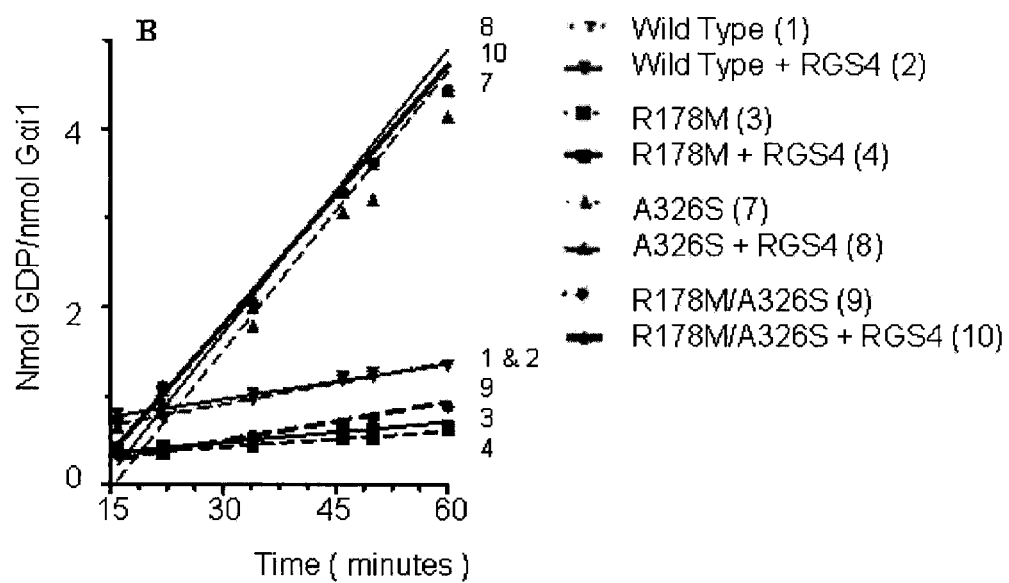

The effect of RGS4 on GTP hydrolysis by WT and mutated $G\alpha_{i1}$ proteins is illustrated in FIG. 2. In this experiment, $G\alpha_{i1}$ proteins were incubated with and without RGS4 in the presence of GDP assay reagents, and plates were read at intervals starting at 15 minutes. The polarization data is shown in FIG. 2A, and in FIG. 2B a subset of the data in the linear region has been converted to GDP formation using a standard curve and normalized to the amount of $G\alpha_{i1}$ protein present. FIG. 2A is complex, and the main observations to point out are as follows: a) The variants with mutations at the catalytic arginine only, R178C and R178M, had lower activity than wild type $G\alpha_{i1}$ and, like wild type, were unaffected by RGS4. These results are expected because the observed GTPase rate is limited by the slow dissociation of GDP from enzyme following the hydrolysis reaction for all of these proteins. b) The A326S variant exhibits a much higher GTPase rate, as would be expected from its higher reported $k_{off\ GDP}$ and is also unaffected by RGS4, presumably because a further increase in GTPase is limited by $k_{off\ GDP}$. c) Most importantly, the two double mutants, R178M/A326S and R178C/A326S had very low basal GTPase activity and much higher activity in the presence of RGS4; the GAP effect on R178M/A326S was greater than with R178C/A326S. The effects of the R178M and A326S mutations, alone and in combination, are shown in more detail in FIG. 2B. The maximum polarization shift resulting from RGS stimulation was 73 mP for R178M/A326S (at 120 min); this is an adequate window for an HTS assay.

GTPase rates for $G\alpha_{i1}$ proteins in the presence and absence of RGS4 are shown in the Table 6.

TABLE 6

| | GTPase rate Rates are in min$^{-1}$ | | GAP |
|---|---|---|---|
| | No RGS4 | +RGS4 | Factor |
| WT | 0.016 | 0.013 | 0.81 |
| R178M | 0.0059 | 0.007 | 1.19 |
| R178C | 0.00038 | 0.00035 | 0.92 |
| A326S | 0.10 | 0.11 | 1.10 |
| R178C/A326S | 0.019 | 0.069 | 3.63 |
| R178M/A326S | 0.015 | 0.097 | 6.47 |

The rates of GTP hydrolysis calculated from the data in FIG. 2A, are shown in Table 6. Note that the observed rates may still be limited by GDP dissociation. However, our hypothesis was that inventors would be able to increase $k_{off\ (GDP)}/k_{cat\ (GTPase)}$—which is 0.03 for WT $G\alpha_{i1}$—only enough to detect 4-fold stimulation by RGS using a steady state GTPase assay.

Example 2

The Specific Combination of R178M and A326S Accelerates GDP Dissociation More than Expected To gain an accurate understanding of how catalysis was affected in mutated $G\alpha_{i1}$ proteins, classic radioassay methods were employed to directly measure GDP dissociation and GTP hydrolysis rates. Single turnover GTP hydrolysis assays, which are not rate-limited by GDP dissociation [Ross, E. M. *Methods Enzymol*, 2002. 344: p. 601-1], were used to measure the intrinsic $k_{cat}$, and GTPγS binding assays were used to measure GDP dissociation. The single turnover assay measures $^{32}P_i$ released from enzyme-bound γ-$^{32}$P-GTP; reactions are terminated before a stoichiometric amount of phosphate is formed. Binding of the non-hydrolyzable GTP analog, GTPγ-$^{35}$S, to $G\alpha_{i1}$ which had been preloaded with GDP was used as a measure of the rate of GDP dissociation; the assumption is that $k_{on}$ for GTPγ-$^{35}$S is much more rapid than $k_{off}$ for GDP.

The results from single turnover GTP hydrolysis assays indicated that, as expected, all of the $G\alpha_{i1}$ variants with a mutation in the catalytic arginine have very low or undetectable levels of GTP hydrolysis, whereas the variant with a single mutation that only affects GDP dissociation, A326S, has a rate similar to wild type $G\alpha_{i1}$ (Table 5). The GTPγ-$^{35}$S binding assays showed that wild type $G\alpha_{i1}$ and the two variants with mutations only at the catalytic site, R178M and R178C, had similar rates of GDP dissociation; whereas introduction of the A326S mutation, either alone or in combination with R178C, caused a three-fold acceleration in GDP dissociation less than would be expected from previous studies. However, when A326 was combined with the methionine substitution at R178 instead of cysteine, the GDP dissociation rate increased more than ten-fold from 0.008 min$^{-1}$ to 0.130 min$^{-1}$ (Table 7). Inventors do not know why the particular combination of R178M and A326S resulted in more rapid GDP release than A326 alone; it is not an additive effect since the singly-mutated R178M variant exhibits wild type GDP dissociation. However, the data is consistent with our steady state GAP assays (Table 5), in which inventors observed a 6.5-fold RGS4 GAP effect with R178M/A326S.

The rates of GTP binding (GDP dissociation) and hydrolysis determined by radioassays are shown in Table 7.

TABLE 7

| Gαi1 | GTP binding (min$^{-1}$) | GTP hydrolysis (min$^{-1}$) |
|---|---|---|
| WT | 0.009 | 1.718 |
| R178M | 0.008 | 0.001 |
| R178C | 0.009 | 0.008 |
| A326S | 0.027 | 1.097 |
| R178M/A326S | 0.130 | 0.000 |
| R178C/A326S | 0.025 | 0.000 |

Inventors also used radiometric GTPase assay methods to confirm the RGS4 GAP effect with $G\alpha_{i1}$ R178M/A326S. In this case, steady state assays were performed since there is no need for the single turnover approach. RGS4 caused a very significant enhancement of GTPase activity (Table 7) for R178M/A326S. Thus, inventors have used two independent methods—radioactive phosphate detection and GDP immunodetection to show that inventors can detect a significant GAP effect for RGS4 using the R178M/A326S variant of $G\alpha_{i1}$.

Example 3

The Gαi1 R178M/A326S Double Mutant is Specifically Recognized by RGS Proteins

A concern about the use of mutated Gα proteins for RGS GAP assays is that the mutations could disrupt the normal specificity that RGS proteins show for the various Gα substrates. To test for this possibility with $G\alpha_{i1}$ R178M/A326S, inventors measured the GAP effects of three additional RGS domains on the R178M/A326S. Inventors used RGS2, which is not expected to have a functional interaction with wild type $G\alpha_{i1}$ in vitro based on multiple previous studies [Heximer et al. *J Biol Chem*, 1999. 274(48): p. 34253-9; and Heximer et al. *Proc Natl Acad Sci U S A*, 1997. 94(26): p. 14389-93], and RGS21, the newest member of the R4 subfamily, which has been shown to bind $G\alpha_{i1}$ [von Buchholtz et al. *Eur J Neurosci*, 2004. 19(6): p. 1535-44] and have a GAP effect on $G\alpha_{i1}$ in single turnover radio assays. In addition, inventors included an RGS21 variant in which a conserved arginine (R126) at the interface of the complex with Gα proteins has been substituted with glutamate. This mutation has been shown to disrupt the functional interaction of RGS21 with $G\alpha_{i1}$. The selectivity of these RGS domains for $G\alpha_{i1}$ is not affected by the R178M/A326S double mutation. RGS4 and wild type RGS21 caused a stimulation of $G\alpha_{i1}$ R178M/A326 GTPase activity of 6.6- and 8.8-fold, respectively, whereas the Gαq-selective RGS2 and the mutated RGS21 had no effect. Though not a comprehensive analysis, these results suggest that the R178M/A326S double mutation to Gα subunits will serve as useful reagents for identifying RGS selective inhibitors and lead to potentially powerful mediators of disease pathways.

All publications cited herein are hereby incorporated by reference in their entirety. In the case of conflict between the present disclosure and the incorporated publications, the present disclosure should control.

While the present invention has now been described and exemplified with some specificity, those skilled in the art will appreciate the various modifications, including variations, additions, and omissions that may be made in what has been described. Accordingly, it is intended that these modifications also be encompassed by the present invention and that the scope of the present invention be limited solely by the broadest interpretation that lawfully can be accorded the appended claims.

We claim:

1. An engineered protein comprising a human Gα protein differing in amino acid sequence from a reference native Gα protein, wherein the difference comprises at least two amino acid substitutions, wherein the substitutions have a net effect of an increase in the GDP dissociation rate and a decrease in the GTP hydrolysis rate, so that the rate of GDP dissociation is no longer rate limiting for catalysis relative to a Gα protein without said amino acid substitutions, wherein said human Gα protein comprises at least two amino acid substitutions corresponding to positions 178 and 326 of SEQ ID NO: 1.

2. The engineered Gα protein of claim 1, wherein the reference Gα protein comprises an amino acid sequence from any one of SEQ ID NOs: 1-20.

3. A kit comprising at least one engineered Gα protein of claim 1.

4. The engineered Gα protein of claim 1, wherein when the engineered Gα protein is in the presence of an multifunctional GTPase-accelerating (RGS) protein, the detectable steady state GTPase activity is increased at least two-fold relative to the GTPase activity of Gα protein in the absence of an RGS protein.

5. A method of using the engineered Gα protein of claim 1, wherein the method comprises incubating the engineered Gα protein in the presence or absence of a protein containing an RGS domain.

6. A method of using the engineered Gα protein of claim 1, wherein the method comprises
   incubating the engineered Gα protein in the presence or absence of a protein containing an RGS domain, wherein the engineered Gα protein differs in amino acid sequence from a reference native Gα protein in at least two amino acid substitutions, wherein the substitutions have a net effect of an increase in the GDP dissociation rate and a decrease in the GTP hydrolysis rate, so that the rate of GDP dissociation is no longer rate limiting for catalysis relative to a Gα protein without said amino acid substitutions.

7. The method of claim 6 further comprising determining GAP activity, wherein when the engineered Gα protein is incubated in the presence of a protein containing an RGS domain, the Gα GTPase activity is stimulated, which is a measure of its GAP activity.

8. A method of detecting the enzymatic GAP activity of an RGS protein by using the engineered Gα protein of claim 1 in the method comprising the steps of:
   a) reacting the engineered Gα protein with guanosine triphosphate (GTP) in the presence and absence of another protein containing an RGS domain;
   b) forming the products guanosine diphosphate (GDP) and phosphate;
   c) detecting the GDP or phosphate as a measure of Gα GTPase activity; and
   d) determining the GAP activity by subtracting the GTPase activity in the absence of the protein containing an RGS domain from the GTPase activity in the presence of the protein containing an RGS domain.

9. A method of detecting the enzymatic GAP activity of an RGS protein by using the engineered Gα protein of claim 1 with the method comprising the steps of:
   a) reacting the engineered Gα protein with guanosine triphosphate (GTP) in the presence and absence of another protein containing an RGS domain;
   b) forming the products guanosine diphosphate (GDP) and phosphate;
   c) contacting the GDP produced in this reaction with a first complex comprising an antibody being specific for the GDP and a fluorescent tracer capable of producing an observable fluorescence;
   d) competitively displacing the tracer of the first complex by the GDP, to generate a second complex GDP-antibody complex and displaced tracer, to directly detect the GDP in the reaction; and
   e) determining the GAP activity by subtracting the GDP formation in the absence of the protein containing an RGS domain from the GDP formation in the presence of the protein containing an RGS domain.

* * * * *

SEQUENCE LISTING

```
<160> NUMBER OF SEQ ID NOS: 61

<210> SEQ ID NO 1
<211> LENGTH: 354
<212> TYPE: PRT
<213> ORGANISM: Homo sapiens

<400> SEQUENCE: 1

Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Ala Gly Tyr Ser Glu Glu
    50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110
```

```
Ala Ala Glu Glu Gly Phe Met Thr Ala Glu Leu Ala Gly Val Ile Lys
            115                 120                 125

Arg Leu Trp Lys Asp Ser Gly Val Gln Ala Cys Phe Asn Arg Ser Arg
        130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
        195                 200                 205

Lys Lys Trp Ile His Cys Phe Glu Gly Val Thr Ala Ile Ile Phe Cys
210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Phe Thr Asp Thr Ser Ile Ile Leu Phe Leu Asn Lys Lys Asp
            260                 265                 270

Leu Phe Glu Glu Lys Ile Lys Lys Ser Pro Leu Thr Ile Cys Tyr Pro
        275                 280                 285

Glu Tyr Ala Gly Ser Asn Thr Tyr Glu Glu Ala Ala Ala Tyr Ile Gln
        290                 295                 300

Cys Gln Phe Glu Asp Leu Asn Lys Arg Lys Asp Thr Lys Glu Ile Tyr
305                 310                 315                 320

Thr His Phe Thr Cys Ala Thr Asp Thr Lys Asn Val Gln Phe Val Phe
                325                 330                 335

Asp Ala Val Thr Asp Val Ile Ile Lys Asn Asn Leu Lys Asp Cys Gly
            340                 345                 350

Leu Phe

<210> SEQ ID NO 2
<211> LENGTH: 355
<212> TYPE: PRT
<213> ORGANISM: Homo sapiens

<400> SEQUENCE: 2

Met Gly Cys Thr Val Ser Ala Glu Asp Lys Ala Ala Glu Arg Ser
1               5                   10                  15

Lys Met Ile Asp Lys Asn Leu Arg Glu Asp Gly Glu Lys Ala Ala Arg
                20                  25                  30

Glu Val Lys Leu Leu Leu Leu Gly Ala Gly Glu Ser Gly Lys Ser Thr
            35                  40                  45

Ile Val Lys Gln Met Lys Ile Ile His Glu Asp Gly Tyr Ser Glu Glu
        50                  55                  60

Glu Cys Arg Gln Tyr Arg Ala Val Val Tyr Ser Asn Thr Ile Gln Ser
65                  70                  75                  80

Ile Met Ala Ile Val Lys Ala Met Gly Asn Leu Gln Ile Asp Phe Ala
                85                  90                  95

Asp Pro Ser Arg Ala Asp Asp Ala Arg Gln Leu Phe Ala Leu Ser Cys
            100                 105                 110

Thr Ala Glu Glu Gln Gly Val Leu Pro Asp Asp Leu Ser Gly Val Ile
        115                 120                 125
```

```
Arg Arg Leu Trp Ala Asp His Gly Val Gln Ala Cys Phe Gly Arg Ser
130                 135                 140

Arg Glu Tyr Gln Leu Asn Asp Ser Ala Ala Tyr Tyr Leu Asn Asp Leu
145                 150                 155                 160

Glu Arg Ile Ala Gln Ser Asp Tyr Ile Pro Thr Gln Gln Asp Val Leu
                165                 170                 175

Arg Thr Arg Val Lys Thr Thr Gly Ile Val Glu Thr His Phe Thr Phe
            180                 185                 190

Lys Asp Leu His Phe Lys Met Phe Asp Val Gly Gly Gln Arg Ser Glu
        195                 200                 205

Arg Lys Lys Trp Ile His Cys Phe Glu Gly Val Thr Ala Ile Ile Phe
    210                 215                 220

Cys Val Ala Leu Ser Ala Tyr Asp Leu Val Leu Ala Glu Asp Glu Glu
225                 230                 235                 240

Met Asn Arg Met His Glu Ser Met Lys Leu Phe Asp Ser Ile Cys Asn
                245                 250                 255

Asn Lys Trp Phe Thr Asp Thr Ser Ile Ile Leu Phe Leu Asn Lys Lys
            260                 265                 270

Asp Leu Phe Glu Glu Lys Ile Thr His Ser Pro Leu Thr Ile Cys Phe
        275                 280                 285

Pro Glu Tyr Thr Gly Ala Asn Lys Tyr Asp Glu Ala Ala Ser Tyr Ile
    290                 295                 300

Gln Ser Lys Phe Glu Asp Leu Asn Lys Arg Lys Asp Thr Lys Glu Ile
305                 310                 315                 320

Tyr Thr His Phe Thr Cys Ala Thr Asp Thr Lys Asn Val Gln Phe Val
                325                 330                 335

Phe Asp Ala Val Thr Asp Val Ile Ile Lys Asn Asn Leu Lys Asp Cys
            340                 345                 350

Gly Leu Phe
        355

<210> SEQ ID NO 3
<211> LENGTH: 354
<212> TYPE: PRT
<213> ORGANISM: Homo sapiens

<400> SEQUENCE: 3

Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Lys
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Asp Gly Tyr Ser Glu Asp
    50                  55                  60

Glu Cys Lys Gln Tyr Lys Val Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Glu Ala Ala Arg Ala Asp Asp Ala Arg Gln Leu Phe Val Leu Ala Gly
            100                 105                 110

Ser Ala Glu Glu Gly Val Met Thr Pro Glu Leu Ala Gly Val Ile Lys
        115                 120                 125

Arg Leu Trp Arg Asp Gly Gly Val Gln Ala Cys Phe Ser Arg Ser Arg
    130                 135                 140
```

```
Glu Tyr Gln Leu Asn Asp Ser Ala Ser Tyr Tyr Leu Asn Asp Leu Asp
145                 150                 155                 160

Arg Ile Ser Gln Ser Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu Tyr Phe Lys Met Phe Asp Val Gly Gly Gln Arg Ser Glu Arg
        195                 200                 205

Lys Lys Trp Ile His Cys Phe Glu Gly Val Thr Ala Ile Ile Phe Cys
    210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Phe Thr Glu Thr Ser Ile Ile Leu Phe Leu Asn Lys Lys Asp
                260                 265                 270

Leu Phe Glu Glu Lys Ile Lys Arg Ser Pro Leu Thr Ile Cys Tyr Pro
            275                 280                 285

Glu Tyr Thr Gly Ser Asn Thr Tyr Glu Glu Ala Ala Ala Tyr Ile Gln
        290                 295                 300

Cys Gln Phe Glu Asp Leu Asn Arg Arg Lys Asp Thr Lys Glu Ile Tyr
305                 310                 315                 320

Thr His Phe Thr Cys Ala Thr Asp Thr Lys Asn Val Gln Phe Val Phe
                325                 330                 335

Asp Ala Val Thr Asp Val Ile Ile Lys Asn Asn Leu Lys Glu Cys Gly
                340                 345                 350

Leu Tyr

<210> SEQ ID NO 4
<211> LENGTH: 381
<212> TYPE: PRT
<213> ORGANISM: Homo sapiens

<400> SEQUENCE: 4

Met Ser Gly Val Val Arg Thr Leu Ser Arg Cys Leu Leu Pro Ala Glu
1               5                   10                  15

Ala Gly Gly Ala Arg Glu Arg Arg Ala Gly Ser Gly Ala Arg Asp Ala
                20                  25                  30

Glu Arg Glu Ala Arg Arg Ser Arg Asp Ile Asp Ala Leu Leu Ala
            35                  40                  45

Arg Glu Arg Arg Ala Val Arg Arg Leu Val Lys Ile Leu Leu Leu Gly
        50                  55                  60

Ala Gly Glu Ser Gly Lys Ser Thr Phe Leu Lys Gln Met Arg Ile Ile
65                  70                  75                  80

His Gly Arg Glu Phe Asp Gln Lys Ala Leu Leu Glu Phe Arg Asp Thr
                85                  90                  95

Ile Phe Asp Asn Ile Leu Lys Gly Ser Arg Val Leu Val Asp Ala Arg
                100                 105                 110

Asp Lys Leu Gly Ile Pro Trp Gln Tyr Ser Glu Asn Glu Lys His Gly
            115                 120                 125

Met Phe Leu Met Ala Phe Glu Asn Lys Ala Gly Leu Pro Val Glu Pro
        130                 135                 140

Ala Thr Phe Gln Leu Tyr Val Pro Ala Leu Ser Ala Leu Trp Arg Asp
145                 150                 155                 160

Ser Gly Ile Arg Glu Ala Phe Ser Arg Arg Ser Glu Phe Gln Leu Gly
```

```
                    165                 170                 175
Glu Ser Val Lys Tyr Phe Leu Asp Asn Leu Asp Arg Ile Gly Gln Leu
                180                 185                 190

Asn Tyr Phe Pro Ser Lys Gln Asp Ile Leu Leu Ala Arg Lys Ala Thr
            195                 200                 205

Lys Gly Ile Val Glu His Asp Phe Val Ile Lys Lys Ile Pro Phe Lys
        210                 215                 220

Met Val Asp Val Gly Gly Gln Arg Ser Gln Arg Gln Lys Trp Phe Gln
225                 230                 235                 240

Cys Phe Asp Gly Ile Thr Ser Ile Leu Phe Met Val Ser Ser Ser Glu
                245                 250                 255

Tyr Asp Gln Val Leu Met Glu Asp Arg Arg Thr Asn Arg Leu Val Glu
            260                 265                 270

Ser Met Asn Ile Phe Glu Thr Ile Val Asn Asn Lys Leu Phe Phe Asn
        275                 280                 285

Val Ser Ile Ile Leu Phe Leu Asn Lys Met Asp Leu Leu Val Glu Lys
    290                 295                 300

Val Lys Thr Val Ser Ile Lys Lys His Phe Pro Asp Phe Arg Gly Asp
305                 310                 315                 320

Pro His Arg Leu Glu Asp Val Gln Arg Tyr Leu Val Gln Cys Phe Asp
                325                 330                 335

Arg Lys Arg Arg Asn Arg Ser Lys Pro Leu Phe His His Phe Thr Thr
            340                 345                 350

Ala Ile Asp Thr Glu Asn Val Arg Phe Val Phe His Ala Val Lys Asp
        355                 360                 365

Thr Ile Leu Gln Glu Asn Leu Lys Asp Ile Met Leu Gln
    370                 375                 380

<210> SEQ ID NO 5
<211> LENGTH: 377
<212> TYPE: PRT
<213> ORGANISM: Homo sapiens

<400> SEQUENCE: 5

Met Ala Asp Phe Leu Pro Ser Arg Ser Val Leu Ser Val Cys Phe Pro
1               5                   10                  15

Gly Cys Leu Leu Thr Ser Gly Glu Ala Glu Gln Gln Arg Lys Ser Lys
            20                  25                  30

Glu Ile Asp Lys Cys Leu Ser Arg Glu Lys Thr Tyr Val Lys Arg Leu
        35                  40                  45

Val Lys Ile Leu Leu Leu Gly Ala Gly Glu Ser Gly Lys Ser Thr Phe
    50                  55                  60

Leu Lys Gln Met Arg Ile Ile His Gly Gln Asp Phe Asp Gln Arg Ala
65                  70                  75                  80

Arg Glu Glu Phe Arg Pro Thr Ile Tyr Ser Asn Val Ile Lys Gly Met
                85                  90                  95

Arg Val Leu Val Asp Ala Arg Glu Lys Leu His Ile Pro Trp Gly Asp
            100                 105                 110

Asn Ser Asn Gln Gln His Gly Asp Lys Met Met Ser Phe Asp Thr Arg
        115                 120                 125

Ala Pro Met Ala Ala Gln Gly Met Val Glu Thr Arg Val Phe Leu Gln
    130                 135                 140

Tyr Leu Pro Ala Ile Arg Ala Leu Trp Ala Asp Ser Gly Ile Gln Asn
145                 150                 155                 160

Ala Tyr Asp Arg Arg Arg Glu Phe Gln Leu Gly Glu Ser Val Lys Tyr
```

```
                        165                 170                 175
Phe Leu Asp Asn Leu Asp Lys Leu Gly Glu Pro Asp Tyr Ile Pro Ser
                180                 185                 190

Gln Gln Asp Ile Leu Leu Ala Arg Arg Pro Thr Lys Gly Ile His Glu
            195                 200                 205

Tyr Asp Phe Glu Ile Lys Asn Val Pro Phe Lys Met Val Asp Val Gly
        210                 215                 220

Gly Gln Arg Ser Glu Arg Lys Arg Trp Phe Cys Phe Asp Ser Val
225                 230                 235                 240

Thr Ser Ile Leu Phe Leu Val Ser Ser Glu Phe Asp Gln Val Leu
                245                 250                 255

Met Glu Asp Arg Leu Thr Asn Arg Leu Thr Glu Ser Leu Asn Ile Phe
            260                 265                 270

Glu Thr Ile Val Asn Asn Arg Val Phe Ser Asn Val Ser Ile Ile Leu
        275                 280                 285

Phe Leu Asn Lys Thr Asp Leu Leu Glu Glu Lys Val Gln Ile Val Ser
    290                 295                 300

Ile Lys Asp Tyr Phe Leu Glu Phe Gly Asp Pro His Cys Leu Arg
305                 310                 315                 320

Asp Val Gln Lys Phe Leu Val Glu Cys Phe Arg Asn Lys Arg Arg Asp
                325                 330                 335

Gln Gln Gln Lys Pro Leu Tyr His His Phe Thr Thr Ala Ile Asn Thr
            340                 345                 350

Glu Asn Ile Arg Leu Val Phe Arg Asp Val Lys Asp Thr Ile Leu His
        355                 360                 365

Asp Asn Leu Lys Gln Leu Met Leu Gln
    370                 375

<210> SEQ ID NO 6
<211> LENGTH: 359
<212> TYPE: PRT
<213> ORGANISM: Homo sapiens

<400> SEQUENCE: 6

Met Thr Leu Glu Ser Ile Met Ala Cys Cys Leu Ser Glu Glu Ala Lys
1               5                   10                  15

Glu Ala Arg Arg Ile Asn Asp Glu Ile Glu Arg Gln Leu Arg Arg Asp
            20                  25                  30

Lys Arg Asp Ala Arg Arg Glu Leu Lys Leu Leu Leu Leu Gly Thr Gly
        35                  40                  45

Glu Ser Gly Lys Ser Thr Phe Ile Lys Gln Met Arg Ile Ile His Gly
    50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Glu Asn Pro Tyr
        115                 120                 125

Val Asp Ala Ile Lys Ser Leu Trp Asn Asp Pro Gly Ile Gln Glu Cys
    130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
```

```
                165                 170                 175
Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
            195                 200                 205

Gln Arg Ser Glu Arg Arg Lys Trp Ile His Cys Phe Glu Asn Val Thr
            210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
            340                 345                 350

Leu Lys Glu Tyr Asn Leu Val
        355

<210> SEQ ID NO 7
<211> LENGTH: 394
<212> TYPE: PRT
<213> ORGANISM: Homo sapiens

<400> SEQUENCE: 7

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
    50                  55                  60

Val Asn Gly Phe Asn Gly Glu Gly Gly Glu Glu Asp Pro Gln Ala Ala
65                  70                  75                  80

Arg Ser Asn Ser Asp Gly Glu Lys Ala Thr Lys Val Gln Asp Ile Lys
                85                  90                  95

Asn Asn Leu Lys Glu Ala Ile Glu Thr Ile Val Ala Ala Met Ser Asn
            100                 105                 110

Leu Val Pro Pro Val Glu Leu Ala Asn Pro Glu Asn Gln Phe Arg Val
        115                 120                 125

Asp Tyr Ile Leu Ser Val Met Asn Val Pro Asp Phe Asp Phe Pro Pro
    130                 135                 140

Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
                165                 170                 175

Tyr Phe Leu Asp Lys Ile Asp Val Ile Lys Gln Ala Asp Tyr Val Pro
```

```
                        180                 185                 190
Ser Asp Gln Asp Leu Leu Arg Cys Arg Val Leu Thr Ser Gly Ile Phe
                195                 200                 205

Glu Thr Lys Phe Gln Val Asp Lys Val Asn Phe His Met Phe Asp Val
        210                 215                 220

Gly Gly Gln Arg Asp Glu Arg Lys Trp Ile Gln Cys Phe Asn Asp
225                 230                 235                 240

Val Thr Ala Ile Ile Phe Val Val Ala Ser Ser Tyr Asn Met Val
                    245                 250                 255

Ile Arg Glu Asp Asn Gln Thr Asn Arg Leu Gln Glu Ala Leu Asn Leu
                260                 265                 270

Phe Lys Ser Ile Trp Asn Asn Arg Trp Leu Arg Thr Ile Ser Val Ile
        275                 280                 285

Leu Phe Leu Asn Lys Gln Asp Leu Leu Ala Glu Lys Val Leu Ala Gly
            290                 295                 300

Lys Ser Lys Ile Glu Asp Tyr Phe Pro Glu Phe Ala Arg Tyr Thr Thr
305                 310                 315                 320

Pro Glu Asp Ala Thr Pro Glu Pro Gly Glu Asp Pro Arg Val Thr Arg
                    325                 330                 335

Ala Lys Tyr Phe Ile Arg Asp Glu Phe Leu Arg Ile Ser Thr Ala Ser
                340                 345                 350

Gly Asp Gly Arg His Tyr Cys Tyr Pro His Phe Thr Cys Ala Val Asp
            355                 360                 365

Thr Glu Asn Ile Arg Arg Val Phe Asn Asp Cys Arg Asp Ile Ile Gln
        370                 375                 380

Arg Met His Leu Arg Gln Tyr Glu Leu Leu
385                 390

<210> SEQ ID NO 8
<211> LENGTH: 355
<212> TYPE: PRT
<213> ORGANISM: Homo sapiens

<400> SEQUENCE: 8

Met Gly Cys Arg Gln Ser Ser Glu Glu Lys Glu Ala Ala Arg Arg Ser
1               5                   10                  15

Arg Arg Ile Asp Arg His Leu Arg Ser Glu Ser Gln Arg Gln Arg Arg
                20                  25                  30

Glu Ile Lys Leu Leu Leu Leu Gly Thr Ser Asn Ser Gly Lys Ser Thr
            35                  40                  45

Ile Val Lys Gln Met Lys Ile Ile His Ser Gly Gly Phe Asn Leu Glu
50                  55                  60

Ala Cys Lys Glu Tyr Lys Pro Leu Ile Ile Tyr Asn Ala Ile Asp Ser
65                  70                  75                  80

Leu Thr Arg Ile Ile Arg Ala Leu Ala Ala Leu Arg Ile Asp Phe His
                85                  90                  95

Asn Pro Asp Arg Ala Tyr Asp Ala Val Gln Leu Phe Ala Leu Thr Gly
            100                 105                 110

Pro Ala Glu Ser Lys Gly Glu Ile Thr Pro Glu Leu Leu Gly Val Met
        115                 120                 125

Arg Arg Leu Trp Ala Asp Pro Gly Ala Gln Ala Cys Phe Ser Arg Ser
    130                 135                 140

Ser Glu Tyr His Leu Glu Asp Asn Ala Ala Tyr Tyr Leu Asn Asp Leu
145                 150                 155                 160

Glu Arg Ile Ala Ala Ala Asp Tyr Ile Pro Thr Val Glu Asp Ile Leu
```

```
                    165                 170                 175
Arg Ser Arg Asp Met Thr Thr Gly Ile Val Glu Asn Lys Phe Thr Phe
            180                 185                 190

Lys Glu Leu Thr Phe Lys Met Val Asp Val Gly Gly Gln Arg Ser Glu
        195                 200                 205

Arg Lys Lys Trp Ile His Cys Phe Glu Gly Val Thr Ala Ile Ile Phe
    210                 215                 220

Cys Val Glu Leu Ser Gly Tyr Asp Leu Lys Leu Tyr Glu Asp Asn Gln
225                 230                 235                 240

Thr Ser Arg Met Ala Glu Ser Leu Arg Leu Phe Asp Ser Ile Cys Asn
            245                 250                 255

Asn Asn Trp Phe Ile Asn Thr Ser Leu Ile Leu Phe Leu Asn Lys Lys
        260                 265                 270

Asp Leu Leu Ala Glu Lys Ile Arg Arg Ile Pro Leu Thr Ile Cys Phe
    275                 280                 285

Pro Glu Tyr Lys Gly Gln Asn Thr Tyr Glu Glu Ala Ala Val Tyr Ile
            290                 295                 300

Gln Arg Gln Phe Glu Asp Leu Asn Arg Asn Lys Glu Thr Lys Glu Ile
305                 310                 315                 320

Tyr Ser His Phe Thr Cys Ala Thr Asp Thr Ser Asn Ile Gln Phe Val
            325                 330                 335

Phe Asp Ala Val Thr Asp Val Ile Ile Gln Asn Asn Leu Lys Tyr Ile
        340                 345                 350

Gly Leu Cys
        355

<210> SEQ ID NO 9
<211> LENGTH: 354
<212> TYPE: PRT
<213> ORGANISM: Homo sapiens

<400> SEQUENCE: 9

Met Gly Cys Thr Leu Ser Ala Glu Glu Arg Ala Ala Leu Glu Arg Ser
1               5                   10                  15

Lys Ala Ile Glu Lys Asn Leu Lys Glu Asp Gly Ile Ser Ala Ala Lys
            20                  25                  30

Asp Val Lys Leu Leu Leu Leu Gly Ala Gly Glu Ser Gly Lys Ser Thr
        35                  40                  45

Ile Val Lys Gln Met Lys Ile Ile His Glu Asp Gly Phe Ser Gly Glu
    50                  55                  60

Asp Val Lys Gln Tyr Lys Pro Val Val Tyr Ser Asn Thr Ile Gln Ser
65                  70                  75                  80

Leu Ala Ala Ile Val Arg Ala Met Asp Thr Leu Gly Ile Glu Tyr Gly
            85                  90                  95

Asp Lys Glu Arg Lys Ala Asp Ala Lys Met Val Cys Asp Val Val Ser
        100                 105                 110

Arg Met Glu Asp Thr Glu Pro Phe Ser Ala Glu Leu Leu Ser Ala Met
    115                 120                 125

Met Arg Leu Trp Gly Asp Ser Gly Ile Gln Glu Cys Phe Asn Arg Ser
            130                 135                 140

Arg Glu Tyr Gln Leu Asn Asp Ser Ala Lys Tyr Tyr Leu Asp Ser Leu
145                 150                 155                 160

Asp Arg Ile Gly Ala Ala Asp Tyr Gln Pro Thr Glu Gln Asp Ile Leu
            165                 170                 175

Arg Thr Arg Val Lys Thr Thr Gly Ile Val Glu Thr His Phe Thr Phe
```

```
                       180                 185                 190
Lys Asn Leu His Phe Arg Leu Phe Asp Val Gly Gly Gln Arg Ser Glu
                195                 200                 205
Arg Lys Lys Trp Ile His Cys Phe Glu Asp Val Thr Ala Ile Ile Phe
            210                 215                 220
Cys Val Ala Leu Ser Gly Tyr Asp Gln Val Leu His Glu Asp Glu Thr
225                 230                 235                 240
Thr Asn Arg Met His Glu Ser Leu Met Leu Phe Asp Ser Ile Cys Asn
                245                 250                 255
Asn Lys Phe Phe Ile Asp Thr Ser Ile Ile Leu Phe Leu Asn Lys Lys
            260                 265                 270
Asp Leu Phe Gly Glu Lys Ile Lys Lys Ser Pro Leu Thr Ile Cys Phe
        275                 280                 285
Pro Glu Tyr Thr Gly Pro Asn Thr Tyr Glu Asp Ala Ala Ala Tyr Ile
        290                 295                 300
Gln Ala Gln Phe Glu Ser Lys Asn Arg Ser Pro Asn Lys Glu Ile Tyr
305                 310                 315                 320
Cys His Met Thr Cys Ala Thr Asp Thr Asn Asn Ile Gln Val Val Phe
                325                 330                 335
Asp Ala Val Thr Asp Ile Ile Ile Ala Asn Asn Leu Arg Gly Cys Gly
            340                 345                 350
Leu Tyr

<210> SEQ ID NO 10
<211> LENGTH: 359
<212> TYPE: PRT
<213> ORGANISM: Homo sapiens

<400> SEQUENCE: 10

Met Thr Leu Glu Ser Met Met Ala Cys Cys Leu Ser Asp Glu Val Lys
1               5                   10                  15
Glu Ser Lys Arg Ile Asn Ala Glu Ile Glu Lys Gln Leu Arg Arg Asp
                20                  25                  30
Lys Arg Asp Ala Arg Arg Glu Leu Lys Leu Leu Leu Leu Gly Thr Gly
            35                  40                  45
Glu Ser Gly Lys Ser Thr Phe Ile Lys Gln Met Arg Ile Ile His Gly
        50                  55                  60
Ala Gly Tyr Ser Glu Glu Asp Lys Arg Gly Phe Thr Lys Leu Val Tyr
65                  70                  75                  80
Gln Asn Ile Phe Thr Ala Met Gln Ala Met Ile Arg Ala Met Glu Thr
                85                  90                  95
Leu Lys Ile Leu Tyr Lys Tyr Glu Gln Asn Lys Ala Asn Ala Leu Leu
            100                 105                 110
Ile Arg Glu Val Asp Val Glu Lys Val Thr Thr Phe Glu His Gln Tyr
        115                 120                 125
Val Ser Ala Ile Lys Thr Leu Trp Glu Asp Pro Gly Ile Gln Glu Cys
        130                 135                 140
Tyr Asp Arg Arg Arg Glu Tyr Gln Leu Ser Asp Ser Ala Lys Tyr Tyr
145                 150                 155                 160
Leu Thr Asp Val Asp Arg Ile Ala Thr Leu Gly Tyr Leu Pro Thr Gln
                165                 170                 175
Gln Asp Val Leu Arg Val Arg Val Pro Thr Thr Gly Ile Ile Glu Tyr
            180                 185                 190
Pro Phe Asp Leu Glu Asn Ile Ile Phe Arg Met Val Asp Val Gly Gly
        195                 200                 205
```

```
Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
                260                 265                 270

Leu Asn Lys Lys Asp Leu Leu Glu Asp Lys Ile Leu Tyr Ser His Leu
            275                 280                 285

Val Asp Tyr Phe Pro Glu Phe Asp Gly Pro Gln Arg Asp Ala Gln Ala
        290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
                340                 345                 350

Leu Lys Glu Tyr Asn Leu Val
            355

<210> SEQ ID NO 11
<211> LENGTH: 374
<212> TYPE: PRT
<213> ORGANISM: Homo sapiens

<400> SEQUENCE: 11

Met Ala Arg Ser Leu Thr Trp Arg Cys Cys Pro Trp Cys Leu Thr Glu
1               5                   10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
130                 135                 140

Arg Ala Tyr Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220
```

```
Asn Val Ile Ala Leu Ile Tyr Leu Ala Ser Leu Ser Glu Tyr Asp Gln
225                 230                 235                 240

Cys Leu Glu Glu Asn Gln Glu Asn Arg Met Lys Glu Ser Leu Ala
            245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
            290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Lys Lys Gly Ala Arg Ser
            325                 330                 335

Arg Arg Leu Phe Ser His Tyr Thr Cys Ala Thr Asp Thr Gln Asn Ile
            340                 345                 350

Arg Lys Val Phe Lys Asp Val Arg Asp Ser Val Leu Ala Arg Tyr Leu
            355                 360                 365

Asp Glu Ile Asn Leu Leu
        370

<210> SEQ ID NO 12
<211> LENGTH: 355
<212> TYPE: PRT
<213> ORGANISM: Homo sapiens

<400> SEQUENCE: 12

Met Ala Gly Cys Cys Cys Leu Ser Ala Glu Glu Lys Glu Ser Gln Arg
1               5                   10                  15

Ile Ser Ala Glu Ile Glu Arg Gln Leu Arg Arg Asp Lys Lys Asp Ala
            20                  25                  30

Arg Arg Glu Leu Lys Leu Leu Leu Leu Gly Thr Gly Glu Ser Gly Lys
        35                  40                  45

Ser Thr Phe Ile Lys Gln Met Arg Ile Ile His Gly Ser Gly Tyr Ser
    50                  55                  60

Asp Glu Asp Arg Lys Gly Phe Thr Lys Leu Val Tyr Gln Asn Ile Phe
65                  70                  75                  80

Thr Ala Met Gln Ala Met Ile Arg Ala Met Asp Thr Leu Arg Ile Gln
                85                  90                  95

Tyr Val Cys Glu Gln Asn Lys Glu Asn Ala Gln Ile Ile Arg Glu Val
            100                 105                 110

Glu Val Asp Lys Val Ser Met Leu Ser Arg Glu Gln Val Glu Ala Ile
        115                 120                 125

Lys Gln Leu Trp Gln Asp Pro Gly Ile Gln Glu Cys Tyr Asp Arg Arg
    130                 135                 140

Arg Glu Tyr Gln Leu Ser Asp Ser Ala Lys Tyr Tyr Leu Thr Asp Ile
145                 150                 155                 160

Asp Arg Ile Ala Thr Pro Ser Phe Val Pro Thr Gln Gln Asp Val Leu
                165                 170                 175

Arg Val Arg Val Pro Thr Thr Gly Ile Ile Glu Tyr Pro Phe Asp Leu
            180                 185                 190

Glu Asn Ile Ile Phe Arg Met Val Asp Val Gly Gly Gln Arg Ser Glu
        195                 200                 205

Arg Arg Lys Trp Ile His Cys Phe Glu Ser Val Thr Ser Ile Ile Phe
    210                 215                 220
```

Leu Val Ala Leu Ser Glu Tyr Asp Gln Val Leu Ala Glu Cys Asp Asn
225                 230                 235                 240

Glu Asn Arg Met Glu Glu Ser Lys Ala Leu Phe Lys Thr Ile Ile Thr
            245                 250                 255

Tyr Pro Trp Phe Leu Asn Ser Ser Val Ile Leu Phe Leu Asn Lys Lys
                260                 265                 270

Asp Leu Leu Glu Glu Lys Ile Met Tyr Ser His Leu Ile Ser Tyr Phe
            275                 280                 285

Pro Glu Tyr Thr Gly Pro Lys Gln Asp Val Arg Ala Ala Arg Asp Phe
        290                 295                 300

Ile Leu Lys Leu Tyr Gln Asp Gln Asn Pro Asp Lys Glu Lys Val Ile
305                 310                 315                 320

Tyr Ser His Phe Thr Cys Ala Thr Asp Thr Asp Asn Ile Arg Phe Val
                325                 330                 335

Phe Ala Ala Val Lys Asp Thr Ile Leu Gln Leu Asn Leu Arg Glu Phe
            340                 345                 350

Asn Leu Val
        355

<210> SEQ ID NO 13
<211> LENGTH: 354
<212> TYPE: PRT
<213> ORGANISM: Homo sapiens

<400> SEQUENCE: 13

Met Gly Cys Thr Leu Ser Ala Glu Glu Arg Ala Ala Leu Glu Arg Ser
1               5                   10                  15

Lys Ala Ile Glu Lys Asn Leu Lys Glu Asp Gly Ile Ser Ala Ala Lys
            20                  25                  30

Asp Val Lys Leu Leu Leu Leu Gly Ala Gly Glu Ser Gly Lys Ser Thr
        35                  40                  45

Ile Val Lys Gln Met Lys Ile Ile His Glu Asp Gly Phe Ser Gly Glu
    50                  55                  60

Asp Val Lys Gln Tyr Lys Pro Val Val Tyr Ser Asn Thr Ile Gln Ser
65                  70                  75                  80

Leu Ala Ala Ile Val Arg Ala Met Asp Thr Leu Gly Ile Glu Tyr Gly
                85                  90                  95

Asp Lys Glu Arg Lys Ala Asp Ala Lys Met Val Cys Asp Val Val Ser
            100                 105                 110

Arg Met Glu Asp Thr Glu Pro Phe Ser Ala Glu Leu Leu Ser Ala Met
        115                 120                 125

Met Arg Leu Trp Gly Asp Ser Gly Ile Gln Glu Cys Phe Asn Arg Ser
    130                 135                 140

Arg Glu Tyr Gln Leu Asn Asp Ser Ala Lys Tyr Tyr Leu Asp Ser Leu
145                 150                 155                 160

Asp Arg Ile Gly Ala Ala Asp Tyr Gln Pro Thr Glu Gln Asp Ile Leu
                165                 170                 175

Arg Thr Arg Val Lys Thr Thr Gly Ile Val Glu Thr His Phe Thr Phe
            180                 185                 190

Lys Asn Leu His Phe Arg Leu Phe Asp Val Gly Gly Gln Arg Ser Glu
        195                 200                 205

Arg Lys Lys Trp Ile His Cys Phe Glu Asp Val Thr Ala Ile Ile Phe
    210                 215                 220

Cys Val Ala Leu Ser Gly Tyr Asp Gln Val Leu His Glu Asp Glu Thr
225                 230                 235                 240

```
Thr Asn Arg Met His Glu Ser Leu Met Leu Phe Asp Ser Ile Cys Asn
            245                 250                 255

Asn Lys Phe Phe Ile Asp Thr Ser Ile Ile Leu Phe Leu Asn Lys Lys
        260                 265                 270

Asp Leu Phe Gly Glu Lys Ile Lys Lys Ser Pro Leu Thr Ile Cys Phe
            275                 280                 285

Pro Glu Tyr Thr Gly Pro Asn Thr Tyr Glu Asp Ala Ala Ala Tyr Ile
        290                 295                 300

Gln Ala Gln Phe Glu Ser Lys Asn Arg Ser Pro Asn Lys Glu Ile Tyr
305                 310                 315                 320

Cys His Met Thr Cys Ala Thr Asp Thr Asn Asn Ile Gln Val Val Phe
                325                 330                 335

Asp Ala Val Thr Asp Ile Ile Ile Ala Asn Asn Leu Arg Gly Cys Gly
                340                 345                 350

Leu Tyr
```

<210> SEQ ID NO 14
<211> LENGTH: 354
<212> TYPE: PRT
<213> ORGANISM: Homo sapiens

<400> SEQUENCE: 14

```
Met Gly Cys Thr Leu Ser Ala Glu Glu Arg Ala Ala Leu Glu Arg Ser
1               5                   10                  15

Lys Ala Ile Glu Lys Asn Leu Lys Glu Asp Gly Ile Ser Ala Ala Lys
            20                  25                  30

Asp Val Lys Leu Leu Leu Leu Gly Ala Gly Glu Ser Gly Lys Ser Thr
        35                  40                  45

Ile Val Lys Gln Met Lys Ile Ile His Glu Asp Gly Phe Ser Gly Glu
    50                  55                  60

Asp Val Lys Gln Tyr Lys Pro Val Val Tyr Ser Asn Thr Ile Gln Ser
65                  70                  75                  80

Leu Ala Ala Ile Val Arg Ala Met Asp Thr Leu Gly Ile Glu Tyr Gly
                85                  90                  95

Asp Lys Glu Arg Lys Ala Asp Ala Lys Met Val Cys Asp Val Val Ser
            100                 105                 110

Arg Met Glu Asp Thr Glu Pro Phe Ser Ala Glu Leu Leu Ser Ala Met
        115                 120                 125

Met Arg Leu Trp Gly Asp Ser Gly Ile Gln Glu Cys Phe Asn Arg Ser
    130                 135                 140

Arg Glu Tyr Gln Leu Asn Asp Ser Ala Lys Tyr Tyr Leu Asp Ser Leu
145                 150                 155                 160

Asp Arg Ile Gly Ala Ala Asp Tyr Gln Pro Thr Glu Gln Asp Ile Leu
                165                 170                 175

Arg Thr Arg Val Lys Thr Thr Gly Ile Val Glu Thr His Phe Thr Phe
            180                 185                 190

Lys Asn Leu His Phe Arg Leu Phe Asp Val Gly Gly Gln Arg Ser Glu
        195                 200                 205

Arg Lys Lys Trp Ile His Cys Phe Glu Asp Val Thr Ala Ile Ile Phe
    210                 215                 220

Cys Val Ala Leu Ser Gly Tyr Asp Gln Val Leu His Glu Asp Glu Thr
225                 230                 235                 240

Thr Asn Arg Met His Glu Ser Leu Lys Leu Phe Asp Ser Ile Cys Asn
                245                 250                 255
```

```
Asn Lys Trp Phe Thr Asp Thr Ser Ile Ile Leu Phe Leu Asn Lys Lys
            260                 265                 270

Asp Ile Phe Glu Glu Lys Ile Lys Lys Ser Pro Leu Thr Ile Cys Phe
            275                 280                 285

Pro Glu Tyr Thr Gly Pro Ser Ala Phe Thr Glu Ala Val Ala Tyr Ile
            290                 295                 300

Gln Ala Gln Tyr Glu Ser Lys Asn Lys Ser Ala His Lys Glu Ile Tyr
305                 310                 315                 320

Thr His Val Thr Cys Ala Thr Asp Thr Asn Asn Ile Gln Phe Val Phe
            325                 330                 335

Asp Ala Val Thr Asp Val Ile Ile Ala Lys Asn Leu Arg Gly Cys Gly
            340                 345                 350

Leu Tyr

<210> SEQ ID NO 15
<211> LENGTH: 354
<212> TYPE: PRT
<213> ORGANISM: Homo sapiens

<400> SEQUENCE: 15

Met Gly Cys Thr Leu Ser Ala Glu Glu Arg Ala Ala Leu Glu Arg Ser
1               5                   10                  15

Lys Ala Ile Glu Lys Asn Leu Lys Glu Asp Gly Ile Ser Ala Ala Lys
            20                  25                  30

Asp Val Lys Leu Leu Leu Leu Gly Ala Gly Glu Ser Gly Lys Ser Thr
            35                  40                  45

Ile Val Lys Gln Met Lys Ile Ile His Glu Asp Gly Phe Ser Gly Glu
        50                  55                  60

Asp Val Lys Gln Tyr Lys Pro Val Val Tyr Ser Asn Thr Ile Gln Ser
65                  70                  75                  80

Leu Ala Ala Ile Val Arg Ala Met Asp Thr Leu Gly Ile Glu Tyr Gly
                85                  90                  95

Asp Lys Glu Arg Lys Ala Asp Ala Lys Met Val Cys Asp Val Val Ser
            100                 105                 110

Arg Met Glu Asp Thr Glu Pro Phe Ser Ala Glu Leu Leu Ser Ala Met
            115                 120                 125

Met Arg Leu Trp Gly Asp Ser Gly Ile Gln Glu Cys Phe Asn Arg Ser
        130                 135                 140

Arg Glu Tyr Gln Leu Asn Asp Ser Ala Lys Tyr Tyr Leu Asp Ser Leu
145                 150                 155                 160

Asp Arg Ile Gly Ala Ala Asp Tyr Gln Pro Thr Glu Gln Asp Ile Leu
                165                 170                 175

Arg Thr Arg Val Lys Thr Thr Gly Ile Val Glu Thr His Phe Thr Phe
            180                 185                 190

Lys Asn Leu His Phe Arg Leu Phe Asp Val Gly Gly Gln Arg Ser Glu
            195                 200                 205

Arg Lys Lys Trp Ile His Cys Phe Glu Asp Val Thr Ala Ile Ile Phe
        210                 215                 220

Cys Val Ala Leu Ser Gly Tyr Asp Gln Val Leu His Glu Asp Glu Thr
225                 230                 235                 240

Thr Asn Arg Met His Glu Ser Leu Met Leu Phe Asp Ser Ile Cys Asn
                245                 250                 255

Asn Lys Phe Phe Ile Asp Thr Ser Ile Ile Leu Phe Leu Asn Lys Lys
            260                 265                 270

Asp Leu Phe Gly Glu Lys Ile Lys Lys Ser Pro Leu Thr Ile Cys Phe
```

Pro Glu Tyr Thr Gly Pro Asn Thr Tyr Glu Asp Ala Ala Tyr Ile
    290                 295                 300

Gln Ala Gln Phe Glu Ser Lys Asn Arg Ser Pro Asn Lys Glu Ile Tyr
305                 310                 315                 320

Cys His Met Thr Cys Ala Thr Asp Thr Asn Asn Ile Gln Val Val Phe
                325                 330                 335

Asp Ala Val Thr Asp Ile Ile Ile Ala Asn Asn Leu Arg Gly Cys Gly
            340                 345                 350

Leu Tyr

<210> SEQ ID NO 16
<211> LENGTH: 381
<212> TYPE: PRT
<213> ORGANISM: Homo sapiens

<400> SEQUENCE: 16

Met Gly Cys Leu Gly Gly Asn Ser Lys Thr Thr Glu Asp Gln Gly Val
1               5                   10                  15

Asp Glu Lys Glu Arg Arg Glu Ala Asn Lys Lys Ile Glu Lys Gln Leu
            20                  25                  30

Gln Lys Glu Arg Leu Ala Tyr Lys Ala Thr His Arg Leu Leu Leu Leu
        35                  40                  45

Gly Ala Gly Glu Ser Gly Lys Ser Thr Ile Val Lys Gln Met Arg Ile
50                  55                  60

Leu His Val Asn Gly Phe Asn Pro Glu Gly Lys Lys Gln Lys Ile Leu
65                  70                  75                  80

Asp Ile Arg Lys Asn Val Lys Asp Ala Ile Val Thr Ile Val Ser Ala
                85                  90                  95

Met Ser Thr Ile Ile Pro Pro Val Pro Leu Ala Asn Pro Glu Asn Gln
            100                 105                 110

Phe Arg Ser Asp Tyr Ile Lys Ser Ile Ala Pro Ile Thr Asp Phe Glu
        115                 120                 125

Tyr Ser Gln Glu Phe Phe Asp His Val Lys Lys Leu Trp Asp Asp Glu
    130                 135                 140

Gly Val Lys Ala Cys Phe Glu Arg Ser Asn Glu Tyr Gln Leu Ile Asp
145                 150                 155                 160

Cys Ala Gln Tyr Phe Leu Glu Arg Ile Asp Ser Val Ser Leu Val Asp
                165                 170                 175

Tyr Thr Pro Thr Asp Gln Asp Leu Leu Arg Cys Arg Val Leu Thr Ser
            180                 185                 190

Gly Ile Phe Glu Thr Arg Phe Gln Val Asp Lys Val Asn Phe His Met
        195                 200                 205

Phe Asp Val Gly Gly Gln Arg Asp Glu Arg Arg Lys Trp Ile Gln Cys
    210                 215                 220

Phe Asn Asp Val Thr Ala Ile Ile Tyr Val Ala Ala Cys Ser Ser Tyr
225                 230                 235                 240

Asn Met Val Ile Arg Glu Asp Asn Asn Thr Asn Arg Leu Arg Glu Ser
                245                 250                 255

Leu Asp Leu Phe Glu Ser Ile Trp Asn Asn Arg Trp Leu Arg Thr Ile
            260                 265                 270

Ser Ile Ile Leu Phe Leu Asn Lys Gln Asp Met Leu Ala Glu Lys Val
        275                 280                 285

Leu Ala Gly Lys Ser Lys Ile Glu Asp Tyr Phe Pro Glu Tyr Ala Asn
    290                 295                 300

Tyr Thr Val Pro Glu Asp Ala Thr Pro Asp Ala Gly Glu Asp Pro Lys
305                 310                 315                 320

Val Thr Arg Ala Lys Phe Phe Ile Arg Asp Leu Phe Leu Arg Ile Ser
                325                 330                 335

Thr Ala Thr Gly Asp Gly Lys His Tyr Cys Tyr Pro His Phe Thr Cys
            340                 345                 350

Ala Val Asp Thr Glu Asn Ile Arg Arg Val Phe Asn Asp Cys Arg Asp
        355                 360                 365

Ile Ile Gln Arg Met His Leu Lys Gln Tyr Glu Leu Leu
    370                 375                 380

<210> SEQ ID NO 17
<211> LENGTH: 354
<212> TYPE: PRT
<213> ORGANISM: Homo sapiens

<400> SEQUENCE: 17

Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Lys
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Asp Gly Tyr Ser Glu Asp
    50                  55                  60

Glu Cys Lys Gln Tyr Lys Val Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Glu Ala Ala Arg Ala Asp Asp Ala Arg Gln Leu Phe Val Leu Ala Gly
            100                 105                 110

Ser Ala Glu Glu Gly Val Met Thr Pro Glu Leu Ala Gly Val Ile Lys
        115                 120                 125

Arg Leu Trp Arg Asp Gly Gly Val Gln Ala Cys Phe Ser Arg Ser Arg
    130                 135                 140

Glu Tyr Gln Leu Asn Asp Ser Ala Ser Tyr Tyr Leu Asn Asp Leu Asp
145                 150                 155                 160

Arg Ile Ser Gln Ser Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu Tyr Phe Lys Met Phe Asp Val Gly Gly Gln Arg Ser Glu Arg
        195                 200                 205

Lys Lys Trp Ile His Cys Phe Glu Gly Val Thr Ala Ile Ile Phe Cys
    210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Phe Thr Glu Thr Ser Ile Ile Leu Phe Leu Asn Lys Lys Asp
            260                 265                 270

Leu Phe Glu Glu Lys Ile Lys Arg Ser Pro Leu Thr Ile Cys Tyr Pro
        275                 280                 285

Glu Tyr Thr Gly Ser Asn Thr Tyr Glu Glu Ala Ala Ala Tyr Ile Gln
    290                 295                 300

Cys Gln Phe Glu Asp Leu Asn Arg Arg Lys Asp Thr Lys Glu Ile Tyr
305                 310                 315                 320

Thr His Phe Thr Cys Ala Thr Asp Thr Lys Asn Val Gln Phe Val Phe
                325                 330                 335

Asp Ala Val Thr Asp Val Ile Ile Lys Asn Asn Leu Lys Glu Cys Gly
            340                 345                 350

Leu Tyr

<210> SEQ ID NO 18
<211> LENGTH: 395
<212> TYPE: PRT
<213> ORGANISM: Homo sapiens

<400> SEQUENCE: 18

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
50                  55                  60

Val Asn Gly Phe Asn Gly Glu Gly Gly Glu Asp Pro Gln Ala Ala
65                  70                  75                  80

Arg Ser Asn Ser Asp Gly Ser Glu Lys Ala Thr Lys Val Gln Asp Ile
            85                  90                  95

Lys Asn Asn Leu Lys Glu Ala Ile Glu Thr Ile Val Ala Ala Met Ser
        100                 105                 110

Asn Leu Val Pro Pro Val Glu Leu Ala Asn Pro Glu Asn Gln Phe Arg
    115                 120                 125

Val Asp Tyr Ile Leu Ser Val Met Asn Val Pro Asp Phe Asp Phe Pro
130                 135                 140

Pro Glu Phe Tyr Glu His Ala Lys Ala Leu Trp Glu Asp Glu Gly Val
145                 150                 155                 160

Arg Ala Cys Tyr Glu Arg Ser Asn Glu Tyr Gln Leu Ile Asp Cys Ala
            165                 170                 175

Gln Tyr Phe Leu Asp Lys Ile Asp Val Ile Lys Gln Ala Asp Tyr Val
        180                 185                 190

Pro Ser Asp Gln Asp Leu Leu Arg Cys Arg Val Leu Thr Ser Gly Ile
    195                 200                 205

Phe Glu Thr Lys Phe Gln Val Asp Lys Val Asn Phe His Met Phe Asp
210                 215                 220

Val Gly Gly Gln Arg Asp Glu Arg Arg Lys Trp Ile Gln Cys Phe Asn
225                 230                 235                 240

Asp Val Thr Ala Ile Ile Phe Val Val Ala Ser Ser Ser Tyr Asn Met
            245                 250                 255

Val Ile Arg Glu Asp Asn Gln Thr Asn Arg Leu Gln Glu Ala Leu Asn
        260                 265                 270

Leu Phe Lys Ser Ile Trp Asn Asn Arg Trp Leu Arg Thr Ile Ser Val
    275                 280                 285

Ile Leu Phe Leu Asn Lys Gln Asp Leu Leu Ala Glu Lys Val Leu Ala
290                 295                 300

Gly Lys Ser Lys Ile Glu Asp Tyr Phe Pro Glu Phe Ala Arg Tyr Thr
305                 310                 315                 320

Thr Pro Glu Asp Ala Thr Pro Glu Pro Gly Glu Asp Pro Arg Val Thr
                    325                 330                 335

Arg Ala Lys Tyr Phe Ile Arg Asp Glu Phe Leu Arg Ile Ser Thr Ala
                340                 345                 350

Ser Gly Asp Gly Arg His Tyr Cys Tyr Pro His Phe Thr Cys Ala Val
            355                 360                 365

Asp Thr Glu Asn Ile Arg Arg Val Phe Asn Asp Cys Arg Asp Ile Ile
        370                 375                 380

Gln Arg Met His Leu Arg Gln Tyr Glu Leu Leu
385                 390                 395

<210> SEQ ID NO 19
<211> LENGTH: 379
<212> TYPE: PRT
<213> ORGANISM: Homo sapiens

<400> SEQUENCE: 19

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
                20                  25                  30

Asp Lys Gln Val Tyr Arg Ala Thr His Arg Leu Leu Leu Leu Gly Ala
            35                  40                  45

Gly Glu Ser Gly Lys Ser Thr Ile Val Lys Gln Met Arg Ile Leu His
        50                  55                  60

Val Asn Gly Phe Asn Gly Asp Glu Lys Ala Thr Lys Val Gln Asp Ile
65                  70                  75                  80

Lys Asn Asn Leu Lys Glu Ala Ile Glu Thr Ile Val Ala Ala Met Ser
                85                  90                  95

Asn Leu Val Pro Pro Val Glu Leu Ala Asn Pro Glu Asn Gln Phe Arg
            100                 105                 110

Val Asp Tyr Ile Leu Ser Val Met Asn Val Pro Asp Phe Asp Phe Pro
        115                 120                 125

Pro Glu Phe Tyr Glu His Ala Lys Ala Leu Trp Glu Asp Glu Gly Val
    130                 135                 140

Arg Ala Cys Tyr Glu Arg Ser Asn Glu Tyr Gln Leu Ile Asp Cys Ala
145                 150                 155                 160

Gln Tyr Phe Leu Asp Lys Ile Asp Val Ile Lys Gln Ala Asp Tyr Val
                165                 170                 175

Pro Ser Asp Gln Asp Leu Leu Arg Cys Arg Val Leu Thr Ser Gly Ile
            180                 185                 190

Phe Glu Thr Lys Phe Gln Val Asp Lys Val Asn Phe His Met Phe Asp
        195                 200                 205

Val Gly Gly Gln Arg Asp Glu Arg Arg Lys Trp Ile Gln Cys Phe Asn
    210                 215                 220

Asp Val Thr Ala Ile Ile Phe Val Val Ala Ser Ser Ser Tyr Asn Met
225                 230                 235                 240

Val Ile Arg Glu Asp Asn Gln Thr Asn Arg Leu Gln Glu Ala Leu Asn
                245                 250                 255

Leu Phe Lys Ser Ile Trp Asn Asn Arg Trp Leu Arg Thr Ile Ser Val
            260                 265                 270

Ile Leu Phe Leu Asn Lys Gln Asp Leu Leu Ala Glu Lys Val Leu Ala
        275                 280                 285

Gly Lys Ser Lys Ile Glu Asp Tyr Phe Pro Glu Phe Ala Arg Tyr Thr
    290                 295                 300

```
Thr Pro Glu Asp Ala Thr Pro Glu Pro Gly Glu Asp Pro Arg Val Thr
305                 310                 315                 320

Arg Ala Lys Tyr Phe Ile Arg Asp Glu Phe Leu Arg Ile Ser Thr Ala
            325                 330                 335

Ser Gly Asp Gly Arg His Tyr Cys Tyr Pro His Phe Thr Cys Ala Val
            340                 345                 350

Asp Thr Glu Asn Ile Arg Arg Val Phe Asn Asp Cys Arg Asp Ile Ile
            355                 360                 365

Gln Arg Met His Leu Arg Gln Tyr Glu Leu Leu
            370                 375
```

<210> SEQ ID NO 20
<211> LENGTH: 380
<212> TYPE: PRT
<213> ORGANISM: Homo sapiens

<400> SEQUENCE: 20

```
Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
            35                  40                  45

Gly Glu Ser Gly Lys Ser Thr Ile Val Lys Gln Met Arg Ile Leu His
        50                  55                  60

Val Asn Gly Phe Asn Gly Asp Ser Glu Lys Ala Thr Lys Val Gln Asp
65                  70                  75                  80

Ile Lys Asn Asn Leu Lys Glu Ala Ile Glu Thr Ile Val Ala Ala Met
                85                  90                  95

Ser Asn Leu Val Pro Pro Val Glu Leu Ala Asn Pro Glu Asn Gln Phe
            100                 105                 110

Arg Val Asp Tyr Ile Leu Ser Val Met Asn Val Pro Asp Phe Asp Phe
        115                 120                 125

Pro Pro Glu Phe Tyr Glu His Ala Lys Ala Leu Trp Glu Asp Glu Gly
130                 135                 140

Val Arg Ala Cys Tyr Glu Arg Ser Asn Glu Tyr Gln Leu Ile Asp Cys
145                 150                 155                 160

Ala Gln Tyr Phe Leu Asp Lys Ile Asp Val Ile Lys Gln Ala Asp Tyr
                165                 170                 175

Val Pro Ser Asp Gln Asp Leu Leu Arg Cys Arg Val Leu Thr Ser Gly
            180                 185                 190

Ile Phe Glu Thr Lys Phe Gln Val Asp Lys Val Asn Phe His Met Phe
        195                 200                 205

Asp Val Gly Gly Gln Arg Asp Glu Arg Arg Lys Trp Ile Gln Cys Phe
210                 215                 220

Asn Asp Val Thr Ala Ile Ile Phe Val Val Ala Ser Ser Ser Tyr Asn
225                 230                 235                 240

Met Val Ile Arg Glu Asp Asn Gln Thr Asn Arg Leu Gln Glu Ala Leu
                245                 250                 255

Asn Leu Phe Lys Ser Ile Trp Asn Asn Arg Trp Leu Arg Thr Ile Ser
            260                 265                 270

Val Ile Leu Phe Leu Asn Lys Gln Asp Leu Leu Ala Glu Lys Val Leu
        275                 280                 285

Ala Gly Lys Ser Lys Ile Glu Asp Tyr Phe Pro Glu Phe Ala Arg Tyr
290                 295                 300
```

```
Thr Thr Pro Glu Asp Ala Thr Pro Glu Pro Gly Asp Pro Arg Val
305                 310                 315                 320

Thr Arg Ala Lys Tyr Phe Ile Arg Asp Glu Phe Leu Arg Ile Ser Thr
            325                 330                 335

Ala Ser Gly Asp Gly Arg His Tyr Cys Tyr Pro His Phe Thr Cys Ala
            340                 345                 350

Val Asp Thr Glu Asn Ile Arg Arg Val Phe Asn Asp Cys Arg Asp Ile
            355                 360                 365

Ile Gln Arg Met His Leu Arg Gln Tyr Glu Leu Leu
            370                 375                 380

<210> SEQ ID NO 21
<211> LENGTH: 116
<212> TYPE: PRT
<213> ORGANISM: Homo sapiens

<400> SEQUENCE: 21

Ser Leu Glu Lys Leu Leu Ala Asn Gln Thr Gly Gln Asn Val Phe Gly
1               5                   10                  15

Ser Phe Leu Lys Ser Glu Phe Ser Glu Glu Asn Ile Glu Phe Trp Leu
            20                  25                  30

Ala Cys Glu Asp Tyr Lys Lys Thr Glu Ser Asp Leu Leu Pro Cys Lys
        35                  40                  45

Ala Glu Glu Ile Tyr Lys Ala Phe Val His Ser Asp Ala Ala Lys Gln
    50                  55                  60

Ile Asn Ile Asp Phe Arg Thr Arg Glu Ser Thr Ala Lys Lys Ile Lys
65                  70                  75                  80

Ala Pro Thr Pro Thr Cys Phe Asp Glu Ala Gln Lys Val Ile Tyr Thr
                85                  90                  95

Leu Met Glu Lys Asp Ser Tyr Pro Arg Phe Leu Lys Ser Asp Ile Tyr
            100                 105                 110

Leu Asn Leu Leu
        115

<210> SEQ ID NO 22
<211> LENGTH: 117
<212> TYPE: PRT
<213> ORGANISM: Homo sapiens

<400> SEQUENCE: 22

Ala Phe Asp Glu Leu Leu Ala Ser Lys Tyr Gly Leu Ala Ala Phe Arg
1               5                   10                  15

Ala Phe Leu Lys Ser Glu Phe Cys Glu Glu Asn Ile Glu Phe Trp Leu
            20                  25                  30

Ala Cys Glu Asp Phe Lys Lys Thr Lys Ser Pro Gln Lys Leu Ser Ser
        35                  40                  45

Lys Ala Arg Lys Ile Tyr Thr Asp Phe Ile Glu Lys Glu Ala Pro Lys
    50                  55                  60

Glu Ile Asn Ile Asp Phe Gln Thr Lys Thr Leu Ile Ala Gln Asn Ile
65                  70                  75                  80

Gln Glu Ala Thr Ser Gly Cys Phe Thr Thr Ala Gln Lys Arg Val Tyr
                85                  90                  95

Ser Leu Met Glu Asn Asn Ser Tyr Pro Arg Phe Leu Glu Ser Glu Phe
            100                 105                 110

Tyr Gln Asp Leu Cys
        115
```

```
<210> SEQ ID NO 23
<211> LENGTH: 116
<212> TYPE: PRT
<213> ORGANISM: Homo sapiens

<400> SEQUENCE: 23

Leu Glu Lys Leu Leu Val His Lys Tyr Gly Leu Ala Val Phe Gln Ala
1               5                   10                  15

Phe Leu Arg Thr Glu Phe Ser Glu Glu Asn Leu Glu Phe Trp Leu Ala
            20                  25                  30

Cys Glu Asp Phe Lys Lys Val Lys Ser Gln Ser Lys Met Ala Ser Lys
        35                  40                  45

Ala Lys Lys Ile Phe Ala Glu Tyr Ile Ala Ile Gln Ala Cys Lys Glu
    50                  55                  60

Val Asn Leu Asp Ser Tyr Thr Arg Glu His Thr Lys Asp Asn Leu Gln
65                  70                  75                  80

Ser Val Thr Arg Gly Cys Phe Asp Leu Ala Gln Lys Arg Ile Phe Gly
                85                  90                  95

Leu Met Glu Lys Asp Ser Tyr Pro Arg Phe Leu Arg Ser Asp Leu Tyr
            100                 105                 110

Leu Asp Leu Ile
        115

<210> SEQ ID NO 24
<211> LENGTH: 117
<212> TYPE: PRT
<213> ORGANISM: Homo sapiens

<400> SEQUENCE: 24

Ser Leu Glu Asn Leu Ile Ser His Glu Cys Gly Leu Ala Ala Phe Lys
1               5                   10                  15

Ala Phe Leu Lys Ser Glu Tyr Ser Glu Glu Asn Ile Asp Phe Trp Ile
            20                  25                  30

Ser Cys Glu Glu Tyr Lys Lys Ile Lys Ser Pro Ser Lys Leu Ser Pro
        35                  40                  45

Lys Ala Lys Lys Ile Tyr Asn Glu Phe Ile Ser Val Gln Ala Thr Lys
    50                  55                  60

Glu Val Asn Leu Asp Ser Cys Thr Arg Glu Glu Thr Ser Arg Asn Met
65                  70                  75                  80

Leu Glu Pro Thr Ile Thr Cys Phe Asp Glu Ala Gln Lys Lys Ile Phe
                85                  90                  95

Asn Leu Met Glu Lys Asp Ser Tyr Arg Arg Phe Leu Lys Ser Arg Phe
            100                 105                 110

Tyr Leu Asp Leu Val
        115

<210> SEQ ID NO 25
<211> LENGTH: 116
<212> TYPE: PRT
<213> ORGANISM: Homo sapiens

<400> SEQUENCE: 25

Leu Asp Lys Leu Leu Gln Asn Asn Tyr Gly Leu Ala Ser Phe Lys Ser
1               5                   10                  15

Phe Leu Lys Ser Glu Phe Ser Glu Glu Asn Leu Glu Phe Trp Ile Ala
            20                  25                  30

Cys Glu Asp Tyr Lys Lys Ile Lys Ser Pro Ala Lys Met Ala Glu Lys
        35                  40                  45
```

```
Ala Lys Gln Ile Tyr Glu Glu Phe Ile Gln Thr Glu Ala Pro Lys Glu
        50                  55                  60

Val Asn Ile Asp His Phe Thr Lys Asp Ile Thr Met Lys Asn Leu Val
 65                  70                  75                  80

Glu Pro Ser Leu Ser Ser Phe Asp Met Ala Gln Lys Arg Ile His Ala
                85                  90                  95

Leu Met Glu Lys Asp Ser Leu Pro Arg Phe Val Arg Ser Glu Phe Tyr
                100                 105                 110

Gln Glu Leu Ile
        115

<210> SEQ ID NO 26
<211> LENGTH: 116
<212> TYPE: PRT
<213> ORGANISM: Homo sapiens

<400> SEQUENCE: 26

Ser Phe Asp Glu Ile Leu Lys Asp Gln Val Gly Arg Asp Gln Phe Leu
 1                   5                  10                  15

Arg Phe Leu Glu Ser Glu Phe Ser Ser Glu Asn Leu Arg Phe Trp Leu
                20                  25                  30

Ala Val Gln Asp Leu Lys Lys Gln Pro Leu Gln Asp Val Ala Lys Arg
                35                  40                  45

Val Glu Glu Ile Trp Gln Glu Phe Leu Ala Pro Gly Ala Pro Ser Ala
        50                  55                  60

Ile Asn Leu Asp Ser His Ser Tyr Glu Ile Thr Ser Gln Asn Val Lys
 65                  70                  75                  80

Asp Gly Gly Arg Tyr Thr Phe Glu Asp Ala Gln Glu His Ile Tyr Lys
                85                  90                  95

Leu Met Lys Ser Asp Ser Tyr Ala Arg Phe Leu Arg Ser Asn Ala Tyr
                100                 105                 110

Gln Asp Leu Leu
        115

<210> SEQ ID NO 27
<211> LENGTH: 116
<212> TYPE: PRT
<213> ORGANISM: Homo sapiens

<400> SEQUENCE: 27

Gly Met Asp Glu Ala Leu Lys Asp Pro Val Gly Arg Glu Gln Phe Leu
 1                   5                  10                  15

Lys Phe Leu Glu Ser Glu Phe Ser Ser Glu Asn Leu Arg Phe Trp Leu
                20                  25                  30

Ala Val Glu Asp Leu Lys Lys Arg Pro Ile Lys Glu Val Pro Ser Arg
                35                  40                  45

Val Gln Glu Ile Trp Gln Glu Phe Leu Ala Pro Gly Ala Pro Ser Ala
        50                  55                  60

Ile Asn Leu Asp Ser Lys Ser Tyr Asp Lys Thr Thr Gln Asn Val Lys
 65                  70                  75                  80

Glu Pro Gly Arg Tyr Thr Phe Glu Asp Ala Gln Glu His Ile Tyr Lys
                85                  90                  95

Leu Met Lys Ser Asp Ser Tyr Pro Arg Phe Ile Arg Ser Ser Ala Tyr
                100                 105                 110

Gln Glu Leu Leu
        115
```

```
<210> SEQ ID NO 28
<211> LENGTH: 117
<212> TYPE: PRT
<213> ORGANISM: Homo sapiens

<400> SEQUENCE: 28

Ser Phe Asp Val Leu Leu Ser His Lys Tyr Gly Val Ala Ala Phe Arg
1               5                   10                  15

Ala Phe Leu Lys Thr Glu Phe Ser Glu Glu Asn Leu Glu Phe Trp Leu
            20                  25                  30

Ala Cys Glu Glu Phe Lys Lys Thr Arg Ser Thr Ala Lys Leu Val Ser
        35                  40                  45

Lys Ala His Arg Ile Phe Glu Glu Phe Val Asp Val Gln Ala Pro Arg
    50                  55                  60

Glu Val Asn Ile Asp Phe Gln Thr Arg Glu Ala Thr Arg Lys Asn Leu
65                  70                  75                  80

Gln Glu Pro Ser Leu Thr Cys Phe Asp Gln Ala Gln Gly Lys Val His
                85                  90                  95

Ser Leu Met Glu Lys Asp Ser Tyr Pro Arg Phe Leu Arg Ser Lys Met
            100                 105                 110

Tyr Leu Asp Leu Leu
        115

<210> SEQ ID NO 29
<211> LENGTH: 116
<212> TYPE: PRT
<213> ORGANISM: Homo sapiens

<400> SEQUENCE: 29

Asn Phe Ser Glu Leu Ile Arg Asp Pro Lys Gly Arg Gln Ser Phe Gln
1               5                   10                  15

Tyr Phe Leu Lys Lys Glu Phe Ser Gly Glu Asn Leu Gly Phe Trp Glu
            20                  25                  30

Ala Cys Glu Asp Leu Lys Tyr Gly Asp Gln Ser Lys Val Lys Glu Lys
        35                  40                  45

Ala Glu Glu Ile Tyr Lys Leu Phe Leu Ala Pro Gly Ala Arg Arg Trp
    50                  55                  60

Ile Asn Ile Asp Gly Lys Thr Met Asp Ile Thr Val Lys Gly Leu Lys
65                  70                  75                  80

His Pro His Arg Tyr Val Leu Asp Ala Ala Gln Thr His Ile Tyr Met
                85                  90                  95

Leu Met Lys Lys Asp Ser Tyr Ala Arg Tyr Leu Lys Ser Pro Ile Tyr
            100                 105                 110

Lys Asp Met Leu
        115

<210> SEQ ID NO 30
<211> LENGTH: 116
<212> TYPE: PRT
<213> ORGANISM: Homo sapiens

<400> SEQUENCE: 30

Ser Leu Glu Asn Leu Leu Glu Asp Pro Glu Gly Val Lys Arg Phe Arg
1               5                   10                  15

Glu Phe Leu Lys Lys Glu Phe Ser Glu Asn Val Leu Phe Trp Leu
            20                  25                  30

Ala Cys Glu Asp Phe Lys Lys Met Gln Asp Lys Thr Gln Met Gln Glu
        35                  40                  45
```

```
Lys Ala Lys Glu Ile Tyr Met Thr Phe Leu Ser Ser Lys Ala Ser Ser
 50                  55                  60

Gln Val Asn Val Glu Gly Gln Ser Arg Leu Asn Glu Lys Ile Leu Glu
 65                  70                  75                  80

Glu Pro His Pro Leu Met Phe Gln Lys Leu Gln Asp Gln Ile Phe Asn
                 85                  90                  95

Leu Met Lys Tyr Asp Ser Tyr Ser Arg Phe Leu Lys Ser Asp Leu Phe
                100                 105                 110

Leu Lys His Lys
            115

<210> SEQ ID NO 31
<211> LENGTH: 116
<212> TYPE: PRT
<213> ORGANISM: Homo sapiens

<400> SEQUENCE: 31

Ser Phe Arg Glu Leu Leu Glu Asp Pro Val Gly Arg Ala His Phe Met
 1               5                  10                  15

Asp Phe Leu Gly Lys Glu Phe Ser Gly Glu Asn Leu Ser Phe Trp Glu
                 20                  25                  30

Ala Cys Glu Glu Leu Arg Tyr Gly Ala Gln Ala Gln Val Pro Thr Leu
             35                  40                  45

Val Asp Ala Val Tyr Glu Gln Phe Leu Ala Pro Gly Ala Ala His Trp
 50                  55                  60

Val Asn Ile Asp Ser Arg Thr Met Glu Gln Thr Leu Glu Gly Leu Arg
 65                  70                  75                  80

Gln Pro His Arg Tyr Val Leu Asp Asp Ala Gln Leu His Ile Tyr Met
                 85                  90                  95

Leu Met Lys Lys Asp Ser Tyr Pro Arg Phe Leu Lys Ser Asp Met Tyr
                100                 105                 110

Lys Ala Leu Leu
            115

<210> SEQ ID NO 32
<211> LENGTH: 118
<212> TYPE: PRT
<213> ORGANISM: Homo sapiens

<400> SEQUENCE: 32

Ser Phe Glu Arg Leu Leu Gln Asp Pro Val Gly Val Arg Tyr Phe Ser
 1               5                  10                  15

Asp Phe Leu Arg Lys Glu Phe Ser Glu Glu Asn Ile Leu Phe Trp Gln
                 20                  25                  30

Ala Cys Glu Tyr Phe Asn His Val Pro Ala His Asp Lys Lys Glu Leu
             35                  40                  45

Ser Tyr Arg Ala Arg Glu Ile Phe Ser Lys Phe Leu Cys Ser Lys Ala
 50                  55                  60

Thr Thr Pro Val Asn Ile Asp Ser Gln Ala Gln Leu Ala Asp Asp Val
 65                  70                  75                  80

Leu Arg Ala Pro His Pro Asp Met Phe Lys Glu Gln Gln Leu Gln Ile
                 85                  90                  95

Phe Asn Leu Met Lys Phe Asp Ser Tyr Thr Arg Phe Leu Lys Ser Pro
                100                 105                 110

Leu Tyr Gln Glu Cys Ile
            115
```

```
<210> SEQ ID NO 33
<211> LENGTH: 117
<212> TYPE: PRT
<213> ORGANISM: Homo sapiens

<400> SEQUENCE: 33

Ser Phe Glu Asn Leu Met Ala Thr Lys Tyr Gly Pro Val Val Tyr Ala
1               5                   10                  15

Ala Tyr Leu Lys Met Glu His Ser Asp Glu Asn Ile Gln Phe Trp Met
            20                  25                  30

Ala Cys Glu Thr Tyr Lys Lys Ile Ala Ser Arg Trp Ser Arg Ile Ser
        35                  40                  45

Arg Ala Lys Lys Leu Tyr Lys Ile Tyr Ile Gln Pro Gln Ser Pro Arg
    50                  55                  60

Glu Ile Asn Ile Asp Ser Ser Thr Arg Glu Thr Ile Ile Arg Asn Ile
65                  70                  75                  80

Gln Glu Pro Thr Glu Thr Cys Phe Glu Glu Ala Gln Lys Ile Val Tyr
                85                  90                  95

Met His Met Glu Arg Asp Ser Tyr Pro Arg Phe Leu Lys Ser Glu Met
            100                 105                 110

Tyr Gln Lys Leu Leu
        115

<210> SEQ ID NO 34
<211> LENGTH: 118
<212> TYPE: PRT
<213> ORGANISM: Homo sapiens

<400> SEQUENCE: 34

Ser Phe Glu Arg Leu Leu Gln Asp Pro Leu Gly Leu Ala Tyr Phe Thr
1               5                   10                  15

Glu Phe Leu Lys Lys Glu Phe Ser Ala Glu Asn Val Thr Phe Trp Lys
            20                  25                  30

Ala Cys Glu Arg Phe Gln Gln Ile Pro Ala Ser Asp Thr Gln Gln Leu
        35                  40                  45

Ala Gln Glu Ala Arg Asn Ile Tyr Gln Glu Phe Leu Ser Ser Gln Ala
    50                  55                  60

Leu Ser Pro Val Asn Ile Asp Arg Gln Ala Trp Leu Gly Glu Glu Val
65                  70                  75                  80

Leu Ala Glu Pro Arg Pro Asp Met Phe Arg Ala Gln Gln Leu Gln Ile
                85                  90                  95

Phe Asn Leu Met Lys Phe Asp Ser Tyr Ala Arg Phe Val Lys Ser Pro
            100                 105                 110

Leu Tyr Arg Glu Cys Leu
        115

<210> SEQ ID NO 35
<211> LENGTH: 117
<212> TYPE: PRT
<213> ORGANISM: Homo sapiens

<400> SEQUENCE: 35

Ser Phe Asp Leu Leu Ser Ser Lys Asn Gly Val Ala Ala Phe His
1               5                   10                  15

Ala Phe Leu Lys Thr Glu Phe Ser Glu Glu Asn Leu Glu Phe Trp Leu
            20                  25                  30

Ala Cys Glu Glu Phe Lys Lys Ile Arg Ser Ala Thr Lys Leu Ala Ser
        35                  40                  45
```

```
Arg Ala His Gln Ile Phe Glu Glu Phe Ile Cys Ser Glu Ala Pro Lys
        50                  55                  60

Glu Val Asn Ile Asp His Glu Thr His Glu Leu Thr Arg Met Asn Leu
 65                  70                  75                  80

Gln Thr Ala Thr Ala Thr Cys Phe Asp Ala Ala Gln Gly Lys Thr Arg
                85                  90                  95

Thr Leu Met Glu Lys Asp Ser Tyr Pro Arg Phe Leu Lys Ser Pro Ala
            100                 105                 110

Tyr Arg Asp Leu Ala
            115

<210> SEQ ID NO 36
<211> LENGTH: 117
<212> TYPE: PRT
<213> ORGANISM: Homo sapiens

<400> SEQUENCE: 36

Asn Phe Asp Lys Met Met Lys Ala Pro Ala Gly Arg Asn Leu Phe Arg
 1               5                  10                  15

Glu Phe Leu Arg Thr Glu Tyr Ser Glu Glu Asn Leu Leu Phe Trp Leu
                20                  25                  30

Ala Cys Glu Asp Leu Lys Lys Glu Gln Asn Lys Lys Val Ile Glu Glu
            35                  40                  45

Lys Ala Arg Met Ile Tyr Glu Asp Tyr Ile Ser Ile Leu Ser Pro Lys
        50                  55                  60

Glu Val Ser Leu Asp Ser Arg Val Arg Glu Val Ile Asn Arg Asn Leu
 65                  70                  75                  80

Leu Asp Pro Asn Pro His Met Tyr Glu Asp Ala Gln Leu Gln Ile Tyr
                85                  90                  95

Thr Leu Met His Arg Asp Ser Phe Pro Arg Phe Leu Asn Ser Gln Ile
            100                 105                 110

Tyr Lys Ser Phe Val
            115

<210> SEQ ID NO 37
<211> LENGTH: 117
<212> TYPE: PRT
<213> ORGANISM: Homo sapiens

<400> SEQUENCE: 37

Ser Phe Asp Lys Leu Leu Ser His Arg Asp Gly Leu Glu Ala Phe Thr
 1               5                  10                  15

Arg Phe Leu Lys Thr Glu Phe Ser Glu Glu Asn Ile Glu Phe Trp Ile
                20                  25                  30

Ala Cys Glu Asp Phe Lys Lys Ser Lys Gly Pro Gln Gln Ile His Leu
            35                  40                  45

Lys Ala Lys Ala Ile Tyr Glu Lys Phe Ile Gln Thr Asp Ala Pro Lys
        50                  55                  60

Glu Val Asn Leu Asp Phe His Thr Lys Glu Val Ile Thr Asn Ser Ile
 65                  70                  75                  80

Thr Gln Pro Thr Leu His Ser Phe Asp Ala Ala Gln Ser Arg Val Tyr
                85                  90                  95

Gln Leu Met Glu Gln Asp Ser Tyr Thr Arg Phe Leu Lys Ser Asp Ile
            100                 105                 110

Tyr Leu Asp Leu Met
            115
```

```
<210> SEQ ID NO 38
<211> LENGTH: 117
<212> TYPE: PRT
<213> ORGANISM: Homo sapiens

<400> SEQUENCE: 38

Ser Phe Asp Lys Leu Met His Ser Pro Ala Gly Arg Ser Val Phe Arg
1               5                   10                  15

Ala Phe Leu Arg Thr Glu Tyr Ser Glu Glu Asn Met Leu Phe Trp Leu
            20                  25                  30

Ala Cys Glu Glu Leu Lys Ala Glu Ala Asn Gln His Val Val Asp Glu
        35                  40                  45

Lys Ala Arg Leu Ile Tyr Glu Asp Tyr Val Ser Ile Leu Ser Pro Lys
    50                  55                  60

Glu Val Ser Leu Asp Ser Arg Val Arg Glu Gly Ile Asn Lys Lys Met
65                  70                  75                  80

Gln Glu Pro Ser Ala His Thr Phe Asp Ala Gln Leu Gln Ile Tyr
                85                  90                  95

Thr Leu Met His Arg Asp Ser Tyr Pro Arg Phe Leu Ser Ser Pro Thr
            100                 105                 110

Tyr Arg Ala Leu Leu
        115

<210> SEQ ID NO 39
<211> LENGTH: 117
<212> TYPE: PRT
<213> ORGANISM: Homo sapiens

<400> SEQUENCE: 39

Ser Phe Asp Lys Leu Met Val Thr Pro Ala Gly Arg Asn Ala Phe Arg
1               5                   10                  15

Glu Phe Leu Arg Thr Glu Phe Ser Glu Glu Asn Met Leu Phe Trp Met
            20                  25                  30

Ala Cys Glu Glu Leu Lys Lys Glu Ala Asn Lys Asn Ile Ile Glu Glu
        35                  40                  45

Lys Ala Arg Ile Ile Tyr Glu Asp Tyr Ile Ser Ile Leu Ser Pro Lys
    50                  55                  60

Glu Val Ser Leu Asp Ser Arg Val Arg Glu Val Ile Asn Arg Asn Met
65                  70                  75                  80

Val Glu Pro Ser Gln His Ile Phe Asp Asp Ala Gln Leu Gln Ile Tyr
                85                  90                  95

Thr Leu Met His Arg Asp Ser Tyr Pro Arg Phe Met Asn Ser Ala Val
            100                 105                 110

Tyr Lys Asp Leu Leu
        115

<210> SEQ ID NO 40
<211> LENGTH: 117
<212> TYPE: PRT
<213> ORGANISM: Homo sapiens

<400> SEQUENCE: 40

Asn Met Asp Thr Leu Leu Ala Asn Gln Ala Gly Leu Asp Ala Phe Arg
1               5                   10                  15

Ile Phe Leu Lys Ser Glu Phe Ser Glu Glu Asn Val Glu Phe Trp Leu
            20                  25                  30

Ala Cys Glu Asp Phe Lys Lys Thr Lys Asn Ala Asp Lys Ile Ala Ser
        35                  40                  45
```

```
Lys Ala Lys Met Ile Tyr Ser Glu Phe Ile Glu Ala Asp Ala Pro Lys
            50                  55                  60
Glu Ile Asn Ile Asp Phe Gly Thr Arg Asp Leu Ile Ser Lys Asn Ile
 65                  70                  75                  80
Ala Glu Pro Thr Leu Lys Cys Phe Asp Glu Ala Gln Lys Leu Ile Tyr
                 85                  90                  95
Cys Leu Met Ala Lys Asp Ser Phe Pro Arg Phe Leu Lys Ser Glu Ile
                100                 105                 110
Tyr Lys Lys Leu Val
            115

<210> SEQ ID NO 41
<211> LENGTH: 100
<212> TYPE: PRT
<213> ORGANISM: Homo sapiens

<400> SEQUENCE: 41

Cys Glu His Ser Gly Asn Lys Leu Trp Lys Asp Ser Val Tyr Phe Trp
 1               5                  10                  15
Phe Asp Leu Gln Ala Tyr His Gln Leu Phe Tyr Gln Glu Thr Leu Gln
                20                  25                  30
Pro Phe Lys Val Cys Lys Gln Ala Gln Tyr Leu Phe Ala Thr Tyr Val
             35                  40                  45
Ala Pro Ser Ala Thr Leu Asp Ile Gly Leu Gln Gln Glu Lys Lys Lys
         50                  55                  60
Glu Ile Tyr Met Lys Ile Gln Pro Pro Phe Glu Asp Leu Phe Asp Thr
 65                  70                  75                  80
Ala Glu Glu Tyr Ile Leu Leu Leu Leu Gly Pro Trp Thr Lys Met
                 85                  90                  95
Val Lys Ser Asp
            100

<210> SEQ ID NO 42
<211> LENGTH: 125
<212> TYPE: PRT
<213> ORGANISM: Homo sapiens

<400> SEQUENCE: 42

Lys Phe Ser Asp Leu Leu Asn Asn Lys Leu Glu Phe Glu His Phe Arg
 1               5                  10                  15
Gln Phe Leu Glu Thr His Ser Ser Ser Arg Ile Leu Cys Ala Asp Arg
                20                  25                  30
His Trp Ser Ser Ser Gly Glu Ile Thr Tyr Arg Asp Arg Asn Gln Arg
             35                  40                  45
Lys Ala Lys Ser Ile Tyr Ile Lys Asn Lys Tyr Leu Asn Lys Lys Tyr
         50                  55                  60
Phe Phe Gly Pro Asn Ser Pro Ala Ser Leu Tyr Gln Gln Asn Gln Val
 65                  70                  75                  80
Met His Leu Ser Gly Gly Trp Gly Lys Ile Leu His Glu Gln Leu Asp
                 85                  90                  95
Ala Pro Val Leu Val Glu Ile Gln Lys His Val Gln Asn Arg Leu Glu
                100                 105                 110
Asn Val Trp Leu Pro Leu Phe Leu Ala Ser Glu Gln Phe
            115                 120                 125

<210> SEQ ID NO 43
<211> LENGTH: 119
<212> TYPE: PRT
```

-continued

<213> ORGANISM: Homo sapiens

<400> SEQUENCE: 43

Glu Phe Glu Ser Val Cys Leu Glu Gln Pro Ile Gly Lys Lys Leu Phe
1               5                   10                  15

Gln Gln Phe Leu Gln Ser Ala Glu Lys His Leu Pro Ala Leu Glu Leu
            20                  25                  30

Trp Lys Asp Ile Glu Asp Tyr Asp Thr Ala Asp Asn Asp Leu Gln Pro
        35                  40                  45

Gln Lys Ala Gln Thr Ile Leu Ala Gln Tyr Leu Asp Pro Gln Ala Lys
    50                  55                  60

Leu Phe Cys Ser Phe Leu Asp Glu Gly Ile Val Ala Lys Phe Lys Glu
65                  70                  75                  80

Gly Pro Val Glu Ile Gln Asp Gly Leu Phe Gln Pro Leu Leu Gln Ala
                85                  90                  95

Thr Leu Ala His Leu Gly Gln Ala Pro Phe Gln Glu Tyr Leu Gly Ser
            100                 105                 110

Leu Tyr Phe Leu Arg Phe Leu
        115

<210> SEQ ID NO 44
<211> LENGTH: 122
<212> TYPE: PRT
<213> ORGANISM: Homo sapiens

<400> SEQUENCE: 44

Thr Phe Glu Lys Ile Phe Ser Gln Lys Leu Gly Tyr Leu Leu Phe Arg
1               5                   10                  15

Asp Phe Cys Leu Asn His Leu Glu Glu Ala Arg Pro Leu Val Glu Phe
            20                  25                  30

Tyr Glu Glu Ile Lys Lys Tyr Glu Lys Leu Glu Thr Glu Glu Glu Arg
        35                  40                  45

Val Ala Arg Ser Arg Glu Ile Phe Asp Ser Tyr Ile Met Lys Glu Leu
    50                  55                  60

Leu Ala Cys Ser His Pro Phe Ser Lys Ser Ala Thr Glu His Val Gln
65                  70                  75                  80

Gly His Leu Gly Lys Lys Gln Val Pro Pro Asp Leu Phe Gln Pro Tyr
                85                  90                  95

Ile Glu Glu Ile Cys Gln Asn Leu Arg Gly Asp Val Phe Gln Lys Phe
            100                 105                 110

Ile Glu Ser Asp Lys Phe Thr Arg Phe Cys
        115                 120

<210> SEQ ID NO 45
<211> LENGTH: 122
<212> TYPE: PRT
<213> ORGANISM: Homo sapiens

<400> SEQUENCE: 45

Thr Phe Asp Lys Ile Phe Asn Gln Lys Ile Gly Phe Leu Leu Phe Lys
1               5                   10                  15

Asp Phe Cys Leu Asn Glu Ile Asn Glu Ala Val Pro Gln Val Lys Phe
            20                  25                  30

Tyr Glu Glu Ile Lys Glu Tyr Glu Lys Leu Asp Asn Glu Asp Arg
        35                  40                  45

Leu Cys Arg Ser Arg Gln Ile Tyr Asp Ala Tyr Ile Met Lys Glu Leu
    50                  55                  60

```
Leu Ser Cys Ser His Pro Phe Ser Lys Gln Ala Val Glu His Val Gln
 65                  70                  75                  80

Ser His Leu Ser Lys Lys Gln Val Thr Ser Thr Leu Phe Gln Pro Tyr
                 85                  90                  95

Ile Glu Glu Ile Cys Glu Ser Leu Arg Gly Asp Ile Phe Gln Lys Phe
            100                 105                 110

Met Glu Ser Asp Lys Phe Thr Arg Phe Cys
            115                 120

<210> SEQ ID NO 46
<211> LENGTH: 121
<212> TYPE: PRT
<213> ORGANISM: Homo sapiens

<400> SEQUENCE: 46

Asp Tyr Ser Ser Leu Cys Asp Lys Gln Pro Ile Gly Arg Arg Leu Phe
  1               5                  10                  15

Arg Gln Phe Cys Asp Thr Lys Pro Thr Leu Lys Arg His Ile Glu Phe
                 20                  25                  30

Leu Asp Ala Val Ala Glu Tyr Glu Val Ala Asp Asp Glu Asp Arg Ser
            35                  40                  45

Asp Cys Gly Leu Ser Ile Leu Asp Arg Phe Phe Asn Asp Lys Leu Ala
         50                  55                  60

Ala Pro Leu Pro Glu Ile Pro Pro Asp Val Val Thr Glu Cys Arg Leu
 65                  70                  75                  80

Gly Leu Lys Glu Glu Asn Pro Ser Lys Lys Ala Phe Glu Glu Cys Thr
                 85                  90                  95

Arg Val Ala His Asn Tyr Leu Arg Gly Glu Pro Phe Glu Glu Tyr Gln
            100                 105                 110

Glu Ser Ser Tyr Phe Ser Gln Phe Leu
            115                 120

<210> SEQ ID NO 47
<211> LENGTH: 120
<212> TYPE: PRT
<213> ORGANISM: Homo sapiens

<400> SEQUENCE: 47

Asp Tyr Cys Ser Leu Cys Asp Lys Gln Pro Ile Gly Arg Leu Leu Phe
  1               5                  10                  15

Arg Gln Phe Cys Glu Thr Arg Pro Gly Leu Glu Cys Tyr Ile Gln Phe
                 20                  25                  30

Leu Asp Ser Val Ala Glu Tyr Glu Val Thr Pro Asp Glu Lys Leu Gly
            35                  40                  45

Glu Lys Gly Lys Glu Ile Met Thr Lys Tyr Leu Thr Pro Lys Ser Pro
         50                  55                  60

Val Phe Ile Ala Gln Val Gly Gln Asp Leu Val Ser Gln Thr Glu Glu
 65                  70                  75                  80

Lys Leu Leu Gln Lys Pro Cys Lys Glu Leu Phe Ser Ala Cys Ala Gln
                 85                  90                  95

Ser Val His Glu Tyr Leu Arg Gly Glu Pro Phe His Glu Tyr Leu Asp
            100                 105                 110

Ser Met Phe Phe Asp Arg Phe Leu
            115                 120

<210> SEQ ID NO 48
<211> LENGTH: 120
<212> TYPE: PRT
```

<213> ORGANISM: Homo sapiens

<400> SEQUENCE: 48

Asp Tyr His Ser Leu Cys Glu Arg Gln Pro Ile Gly Arg Leu Leu Phe
1               5                   10                  15

Arg Glu Phe Cys Ala Thr Arg Pro Glu Leu Ser Arg Cys Val Ala Phe
            20                  25                  30

Leu Asp Gly Val Ala Glu Tyr Glu Val Thr Pro Asp Asp Lys Arg Lys
        35                  40                  45

Ala Cys Gly Arg Gln Leu Thr Gln Asn Phe Leu Ser His Thr Gly Pro
    50                  55                  60

Asp Leu Ile Pro Glu Val Pro Arg Gln Leu Val Thr Asn Cys Thr Gln
65                  70                  75                  80

Arg Leu Glu Gln Gly Pro Cys Lys Asp Leu Phe Gln Glu Leu Thr Arg
                85                  90                  95

Leu Thr His Glu Tyr Leu Ser Val Ala Pro Phe Ala Asp Tyr Leu Asp
            100                 105                 110

Ser Ile Tyr Phe Asn Arg Phe Leu
        115                 120

<210> SEQ ID NO 49
<211> LENGTH: 122
<212> TYPE: PRT
<213> ORGANISM: Homo sapiens

<400> SEQUENCE: 49

Asn Phe His Ser Leu Cys Glu Gln Gln Pro Ile Gly Arg Arg Leu Phe
1               5                   10                  15

Arg Asp Phe Leu Ala Thr Val Pro Thr Phe Arg Lys Ala Ala Thr Phe
            20                  25                  30

Leu Glu Asp Val Gln Asn Trp Glu Leu Ala Glu Gly Pro Thr Lys
        35                  40                  45

Asp Ser Ala Leu Gln Gly Leu Val Ala Thr Cys Ala Ser Ala Pro Ala
    50                  55                  60

Pro Gly Asn Pro Gln Pro Phe Leu Ser Gln Ala Val Ala Thr Lys Cys
65                  70                  75                  80

Gln Ala Ala Thr Thr Glu Glu Arg Val Ala Val Thr Leu Ala
                85                  90                  95

Lys Ala Glu Ala Met Ala Phe Leu Gln Glu Gln Pro Phe Lys Asp Phe
            100                 105                 110

Val Thr Ser Ala Phe Tyr Asp Lys Phe Leu
        115                 120

<210> SEQ ID NO 50
<211> LENGTH: 141
<212> TYPE: PRT
<213> ORGANISM: Homo sapiens

<400> SEQUENCE: 50

Pro Leu Asp Ser Ile Leu Val Asp Asn Val Ala Leu Gln Phe Phe Met
1               5                   10                  15

Asp Tyr Met Gln Gln Thr Gly Gly Gln Ala His Leu Phe Phe Trp Met
            20                  25                  30

Thr Val Glu Gly Tyr Arg Val Thr Ala Gln Gln Leu Glu Val Leu
        35                  40                  45

Leu Ser Arg Gln Arg Asp Gly His Gln Thr Asn Gln Thr Lys Gly
    50                  55                  60

```
Leu Leu Arg Ala Ala Ala Val Gly Ile Tyr Glu Gln Tyr Leu Ser Glu
 65                  70                  75                  80

Lys Ala Ser Pro Arg Val Thr Val Asp Asp Tyr Leu Val Ala Lys Leu
                 85                  90                  95

Ala Asp Thr Leu Asn His Glu Asp Pro Thr Pro Glu Ile Phe Asp Asp
            100                 105                 110

Ile Gln Arg Lys Val Tyr Glu Leu Met Leu Arg Asp Glu Arg Phe Tyr
        115                 120                 125

Pro Ser Phe Arg Gln Asn Ala Leu Tyr Val Arg Met Leu
    130                 135                 140

<210> SEQ ID NO 51
<211> LENGTH: 163
<212> TYPE: PRT
<213> ORGANISM: Homo sapiens

<400> SEQUENCE: 51

Ser Pro Leu Val Pro Phe Leu Gln Lys Phe Ala Glu Pro Arg Asn Lys
  1               5                  10                  15

Lys Pro Ser Val Leu Lys Leu Glu Leu Lys Gln Ile Arg Glu Gln Gln
                 20                  25                  30

Asp Leu Leu Phe Arg Phe Met Asn Phe Leu Lys Gln Glu Gly Ala Val
            35                  40                  45

His Val Leu Gln Phe Cys Leu Thr Val Glu Glu Phe Asn Asp Arg Ile
        50                  55                  60

Leu Arg Pro Glu Leu Ser Asn Asp Glu Met Leu Ser Leu His Glu Glu
 65                  70                  75                  80

Leu Gln Lys Ile Tyr Lys Thr Tyr Cys Leu Asp Glu Ser Ile Asp Lys
                 85                  90                  95

Ile Arg Phe Asp Pro Phe Ile Val Glu Ile Gln Arg Ile Ala Glu
            100                 105                 110

Gly Pro Tyr Ile Asp Val Val Lys Leu Gln Thr Met Arg Cys Leu Phe
        115                 120                 125

Glu Ala Tyr Glu His Val Leu Ser Leu Leu Gly Asn Val Phe Thr Pro
    130                 135                 140

Met Phe Cys His Ser Asp Glu Tyr Phe Arg Gln Leu Leu Arg Gly Ala
145                 150                 155                 160

Glu Ser Pro

<210> SEQ ID NO 52
<211> LENGTH: 115
<212> TYPE: PRT
<213> ORGANISM: Homo sapiens

<400> SEQUENCE: 52

Gln Phe Glu Asp Ile Leu Ala Asn Thr Phe Tyr Arg Glu His Phe Gly
  1               5                  10                  15

Met Tyr Met Glu Arg Met Asp Lys Arg Ala Leu Ile Ser Phe Trp Glu
                 20                  25                  30

Ser Val Glu His Leu Lys Asn Ala Asn Lys Asn Glu Ile Pro Gln Leu
            35                  40                  45

Val Gly Glu Ile Tyr Gln Asn Phe Phe Val Glu Ser Lys Glu Ile Ser
        50                  55                  60

Val Glu Lys Ser Leu Tyr Lys Glu Ile Gln Gln Cys Leu Val Gly Asn
 65                  70                  75                  80

Lys Gly Ile Glu Val Phe Tyr Lys Ile Gln Glu Asp Val Tyr Glu Thr
                 85                  90                  95
```

```
Leu Lys Asp Arg Tyr Tyr Pro Ser Phe Ile Val Ser Asp Leu Tyr Glu
            100                 105                 110

Lys Leu Leu
        115

<210> SEQ ID NO 53
<211> LENGTH: 124
<212> TYPE: PRT
<213> ORGANISM: Homo sapiens

<400> SEQUENCE: 53

Ser Leu His Ser Leu Leu Asp Asp Gln Asp Gly Ile Ser Leu Phe Arg
1               5                   10                  15

Thr Phe Leu Lys Gln Glu Gly Cys Ala Asp Leu Leu Asp Phe Trp Phe
            20                  25                  30

Ala Cys Thr Gly Phe Arg Lys Leu Glu Pro Cys Asp Ser Asn Glu Glu
            35                  40                  45

Lys Arg Leu Lys Leu Ala Arg Ala Ile Tyr Arg Lys Tyr Ile Leu Asp
        50                  55                  60

Asn Asn Gly Ile Val Ser Arg Gln Thr Lys Pro Ala Thr Lys Ser Phe
65                  70                  75                  80

Ile Lys Gly Cys Ile Met Lys Gln Leu Ile Asp Pro Ala Met Phe Asp
                85                  90                  95

Gln Ala Gln Thr Glu Ile Gln Ala Thr Met Glu Glu Asn Thr Tyr Pro
            100                 105                 110

Ser Phe Leu Lys Ser Asp Ile Tyr Leu Glu Tyr Thr
        115                 120

<210> SEQ ID NO 54
<211> LENGTH: 120
<212> TYPE: PRT
<213> ORGANISM: Homo sapiens

<400> SEQUENCE: 54

Ser Leu His Ser Leu Gly Asp Gln Asp Gly Ala Tyr Leu Phe Arg
1               5                   10                  15

Thr Phe Leu Glu Arg Glu Lys Cys Val Asp Thr Leu Asp Phe Trp Phe
            20                  25                  30

Ala Cys Asn Gly Phe Arg Gln Met Asn Leu Lys Asp Thr Lys Thr Leu
            35                  40                  45

Arg Val Ala Lys Ala Ile Tyr Lys Arg Tyr Ile Glu Asn Asn Ser Ile
        50                  55                  60

Val Ser Lys Gln Leu Lys Pro Ala Thr Lys Thr Tyr Ile Arg Asp Gly
65                  70                  75                  80

Ile Lys Lys Gln Gln Ile Asp Ser Ile Met Phe Asp Gln Ala Gln Thr
                85                  90                  95

Glu Ile Gln Ser Val Met Glu Glu Asn Ala Tyr Gln Met Phe Leu Thr
            100                 105                 110

Ser Asp Ile Tyr Leu Glu Tyr Val
        115                 120

<210> SEQ ID NO 55
<211> LENGTH: 173
<212> TYPE: PRT
<213> ORGANISM: Homo sapiens

<400> SEQUENCE: 55

Thr Leu Glu Gln Val Leu His Asp Thr Ile Val Leu Pro Tyr Phe Ile
```

```
                 1               5                  10                 15
Gln Phe Met Glu Leu Arg Arg Met Glu His Leu Val Lys Phe Trp Leu
                20                  25                 30

Glu Ala Glu Ser Phe His Ser Thr Thr Trp Ser Arg Ile Arg Ala His
                35                  40                 45

Ser Leu Asn Thr Met Lys Gln Ser Ser Leu Ala Glu Pro Val Ser Pro
                50                  55                 60

Ser Lys Lys His Glu Thr Thr Ala Ser Phe Leu Thr Asp Ser Leu Asp
65                  70                  75                 80

Lys Arg Leu Glu Asp Ser Gly Ser Ala Gln Leu Phe Met Thr His Ser
                85                  90                 95

Glu Gly Ile Asp Leu Asn Asn Arg Thr Asn Ser Thr Gln Asn His Leu
                100                 105                110

Leu Leu Ser Gln Glu Cys Asp Ser Ala His Ser Leu Arg Leu Glu Met
                115                 120                125

Ala Arg Ala Gly Thr His Gln Val Ser Met Glu Thr Gln Glu Ser Ser
                130                 135                140

Ser Thr Leu Thr Val Ala Ser Arg Asn Ser Pro Ala Ser Pro Leu Lys
145                 150                 155                160

Glu Leu Ser Gly Lys Leu Met Lys Ser Ile Glu Gln Asp
                165                 170
```

<210> SEQ ID NO 56
<211> LENGTH: 127
<212> TYPE: PRT
<213> ORGANISM: Homo sapiens

<400> SEQUENCE: 56

```
Tyr Leu Ala Asp Ile Leu Phe Cys Glu Ser Ala Leu Phe Tyr Phe Ser
1               5                   10                 15

Glu Tyr Met Glu Lys Glu Asp Ala Val Asn Ile Leu Gln Phe Trp Leu
                20                  25                 30

Ala Ala Asp Asn Phe Gln Ser Gln Leu Ala Ala Lys Lys Gly Gln Tyr
                35                  40                 45

Asp Gly Gln Glu Ala Gln Asn Asp Ala Met Ile Leu Tyr Asp Lys Tyr
                50                  55                 60

Phe Ser Leu Gln Ala Thr His Pro Leu Gly Phe Asp Asp Val Val Arg
65                  70                  75                 80

Leu Glu Ile Glu Ser Asn Ile Cys Arg Glu Gly Gly Pro Leu Pro Asn
                85                  90                 95

Cys Phe Thr Thr Pro Leu Arg Gln Ala Trp Thr Thr Met Glu Lys Val
                100                 105                110

Phe Leu Pro Gly Phe Leu Ser Ser Asn Leu Tyr Tyr Lys Tyr Leu
                115                 120                125
```

<210> SEQ ID NO 57
<211> LENGTH: 170
<212> TYPE: PRT
<213> ORGANISM: Homo sapiens

<400> SEQUENCE: 57

```
Asn Ser Gln Phe Gln Ser Leu Glu Gln Val Lys Arg Arg Pro Ala His
1               5                   10                 15

Leu Met Ala Leu Leu Gln His Val Ala Leu Gln Phe Glu Pro Gly Pro
                20                  25                 30

Leu Leu Cys Cys Leu His Ala Asp Met Leu Gly Ser Leu Gly Pro Lys
                35                  40                 45
```

```
Glu Ala Lys Lys Ala Phe Leu Asp Phe Tyr His Ser Phe Leu Glu Lys
     50                  55                  60
Thr Ala Val Leu Arg Val Pro Val Pro Asn Val Ala Phe Glu Leu
 65                  70                  75                  80
Asp Arg Thr Arg Ala Asp Leu Ile Ser Glu Asp Val Gln Arg Arg Phe
                 85                  90                  95
Val Gln Glu Val Val Gln Ser Gln Gln Val Ala Val Gly Arg Gln Leu
                100                 105                 110
Glu Asp Phe Arg Ser Lys Arg Leu Met Gly Met Thr Pro Trp Glu Gln
            115                 120                 125
Glu Leu Ala Gln Leu Glu Ala Trp Val Gly Arg Asp Arg Ala Ser Tyr
        130                 135                 140
Glu Ala Arg Glu Arg His Val Ala Glu Arg Leu Leu Met His Leu Glu
145                 150                 155                 160
Glu Met Gln His Thr Ile Ser Thr Asp Glu
                165                 170
```

```
<210> SEQ ID NO 58
<211> LENGTH: 120
<212> TYPE: PRT
<213> ORGANISM: Homo sapiens

<400> SEQUENCE: 58

Asp Leu Glu Lys Leu Lys Ser Arg Pro Ala His Leu Gly Val Phe Leu
  1               5                  10                  15
Arg Tyr Ile Phe Ser Gln Ala Asp Pro Ser Pro Leu Leu Phe Tyr Leu
                 20                  25                  30
Cys Ala Glu Val Tyr Gln Gln Ala Ser Pro Lys Asp Ser Arg Ser Leu
             35                  40                  45
Gly Lys Asp Ile Trp Asn Ile Phe Leu Glu Lys Asn Ala Pro Leu Arg
         50                  55                  60
Val Lys Ile Pro Glu Met Leu Gln Ala Glu Ile Asp Ser Arg Leu Arg
 65                  70                  75                  80
Asn Ser Glu Asp Ala Arg Gly Val Leu Cys Glu Ala Gln Glu Ala Ala
                 85                  90                  95
Met Pro Glu Ile Gln Glu Gln Ile His Asp Tyr Arg Thr Lys Arg Thr
                100                 105                 110
Leu Gly Leu Gly Ser Leu Tyr Gly
            115                 120
```

```
<210> SEQ ID NO 59
<211> LENGTH: 174
<212> TYPE: PRT
<213> ORGANISM: Homo sapiens

<400> SEQUENCE: 59

Cys Ser Cys Phe Gln Ser Ile Glu Leu Leu Lys Ser Arg Pro Ala His
  1               5                  10                  15
Leu Ala Val Phe Leu His His Val Val Ser Gln Phe Asp Pro Ala Thr
                 20                  25                  30
Leu Leu Cys Tyr Leu Tyr Ser Asp Leu Tyr Lys His Thr Asn Ser Lys
             35                  40                  45
Glu Thr Arg Arg Ile Phe Leu Glu Phe His Gln Phe Leu Asp Arg
         50                  55                  60
Ser Ala His Leu Lys Val Ser Val Pro Asp Glu Met Ser Ala Asp Leu
 65                  70                  75                  80
```

```
Glu Lys Arg Arg Pro Glu Leu Ile Pro Glu Asp Leu His Arg His Tyr
                85                  90                  95

Ile Gln Thr Met Gln Glu Arg Val His Pro Glu Val Gln Arg His Leu
            100                 105                 110

Glu Asp Phe Arg Gln Lys Arg Ser Met Gly Leu Thr Leu Ala Glu Ser
        115                 120                 125

Glu Leu Thr Lys Leu Asp Ala Glu Arg Asp Lys Asp Arg Leu Thr Leu
    130                 135                 140

Glu Lys Glu Arg Thr Cys Ala Glu Gln Ile Val Ala Lys Ile Glu Glu
145                 150                 155                 160

Val Leu Met Thr Ala Gln Ala Val Glu Glu Asp Lys Ser Ser
                165                 170

<210> SEQ ID NO 60
<211> LENGTH: 354
<212> TYPE: PRT
<213> ORGANISM: Artificial
<220> FEATURE:
<223> OTHER INFORMATION: R178M A326S double mutant of SEQ ID 1

<400> SEQUENCE: 60

Met Gly Cys Thr Leu Ser Ala Glu Asp Lys Ala Ala Val Glu Arg Ser
1               5                   10                  15

Lys Met Ile Asp Arg Asn Leu Arg Glu Asp Gly Glu Lys Ala Ala Arg
            20                  25                  30

Glu Val Lys Leu Leu Leu Leu Gly Ala Gly Glu Ser Gly Lys Ser Thr
        35                  40                  45

Ile Val Lys Gln Met Lys Ile Ile His Glu Ala Gly Tyr Ser Glu Glu
    50                  55                  60

Glu Cys Lys Gln Tyr Lys Ala Val Val Tyr Ser Asn Thr Ile Gln Ser
65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
        115                 120                 125

Arg Leu Trp Lys Asp Ser Gly Val Gln Ala Cys Phe Asn Arg Ser Arg
    130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Met Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
        195                 200                 205

Lys Lys Trp Ile His Cys Phe Glu Gly Val Thr Ala Ile Ile Phe Cys
    210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Phe Thr Asp Thr Ser Ile Ile Leu Phe Leu Asn Lys Lys Asp
            260                 265                 270

Leu Phe Glu Glu Lys Ile Lys Lys Ser Pro Leu Thr Ile Cys Tyr Pro
```

-continued

```
                       275                 280                 285
Glu Tyr Ala Gly Ser Asn Thr Tyr Glu Glu Ala Ala Tyr Ile Gln
                290                 295                 300

Cys Gln Phe Glu Asp Leu Asn Lys Arg Lys Asp Thr Lys Glu Ile Tyr
305                 310                 315                 320

Thr His Phe Thr Cys Ser Thr Asp Thr Lys Asn Val Gln Phe Val Phe
                    325                 330                 335

Asp Ala Val Thr Asp Val Ile Ile Lys Asn Asn Leu Lys Asp Cys Gly
                340                 345                 350

Leu Phe
```

<210> SEQ ID NO 61
<211> LENGTH: 1065
<212> TYPE: DNA
<213> ORGANISM: Homo sapiens

<400> SEQUENCE: 61

```
atgggctgca cgctgagcgc cgaggacaag gcggcggtgg agcggagtaa gatgatcgac      60
cgcaacctcc gtgaggacgg cgagaaggcg gcgcgcgagg tcaagctgct gctgctcggt     120
gctggtgaat ctggtaaaag tacaattgtg aagcagatga aaattatcca tgaagctggt     180
tattcagaag aggagtgtaa acaatacaaa gcagtggtct acagtaacac catccagtca     240
attattgcta tcattagggc tatggggagg ttgaagatag actttggtga ctcagcccgg     300
gcggatgatg cacgccaact ctttgtgcta gctggagctg ctgaagaagg ctttatgact     360
gcagaacttg ctggagttat aaagagattg tggaaagata gtggtgtaca agcctgtttc     420
aacagatccc gagagtacca gcttaatgat tctgcagcat actatttgaa tgacttggac     480
agaatagctc aaccaaatta catcccgact caacaagatg ttctcagaac tagagtgaaa     540
actacaggaa ttgttgaaac ccatttttact ttcaaagatc ttcattttaa aatgtttgat     600
gtgggaggtc agagatctga gcggaagaag tggattcatt gcttcgaagg agtgacggcg     660
atcatcttct gtgtagcact gagtgactac gacctggttc tagctgaaga tgaagaaatg     720
aaccgaatgc atgaaagcat gaaattgttt gacagcatat gtaacaacaa gtggtttaca     780
gatacatcca ttatactttt tctaaacaag aaggatctct ttgaagaaaa aatcaaaaag     840
agccctctca ctatatgcta tccagaatat gcaggatcaa acacatatga agaggcagct     900
gcatatattc aatgtcagtt tgaagacctc aataaaagaa aggacacaaa ggaaatatac     960
acccacttca catgtgccac agatactaag aatgtgcagt ttgtttttga tgctgtaaca    1020
gatgtcatca taaaaaataa tctaaaagat tgtggtctct tttaa                    1065
```